(12) United States Patent
Wei

(10) Patent No.: US 7,468,253 B2
(45) Date of Patent: Dec. 23, 2008

(54) METHOD FOR MULTIPLE CHEMOKINE RECEPTOR SCREENING FOR ANTAGONISTS USING RAM ASSAY

(75) Inventor: Zheng Wei, Redwood City, CA (US)

(73) Assignee: Chemocentryx, Inc., Mt. View, CA (US)

( * ) Notice: Subject to any disclaimer, the term of this patent is extended or adjusted under 35 U.S.C. 154(b) by 455 days.

(21) Appl. No.: 10/630,180

(22) Filed: Jul. 30, 2003

(65) Prior Publication Data

US 2004/0023286 A1    Feb. 5, 2004

Related U.S. Application Data

(63) Continuation-in-part of application No. 10/154,399, filed on May 22, 2002, now Pat. No. 7,282,338.

(60) Provisional application No. 60/296,682, filed on Jun. 7, 2001.

(51) Int. Cl.
*G01N 33/566* (2006.01)
*G01N 33/567* (2006.01)
*C07K 14/52* (2006.01)
*C12M 1/00* (2006.01)

(52) U.S. Cl. .................. 435/7.1; 435/7.2; 435/7.21; 530/350

(58) Field of Classification Search ................ None
See application file for complete search history.

(56) References Cited

U.S. PATENT DOCUMENTS

| 6,448,054 | B1 | 9/2002 | Poznansky et al. |
| 6,451,522 | B2 | 9/2002 | LaRosa |
| 6,689,570 | B2 | 2/2004 | Andrew |
| 6,884,574 | B2 | 4/2005 | Andrew |
| 2003/0166143 | A1 | 9/2003 | Klein et al. |

FOREIGN PATENT DOCUMENTS

| WO | WO 97/31949 | 9/1997 |
| WO | WO 98/09171 | 3/1998 |

OTHER PUBLICATIONS

* Ausubel, F.M., R. Brent, R.E. Kingston, D.D. Moore, et al. 1987. Current protocols in molecular biology. John Wiley & Sons, New York.

Bacon, K.B., R.D. Camp, F.M. Cunningham, and P.M. Woollard. 1988. Contrasting in vitro lymphocyte chemotactic activity of the hydroxyl enantiomers of 12-hydroxy-5,8,10,14-eicosatetraenoic acid. *Br J Pharmacol.* 95:966-74.
* Baggiolini et al., Annu. Rev. Immunol, 15: 675-705 (1997).
* Baggiolini et al., Advances in Immunology, 55:97-179 (1994).
* Deng, et al., *Nature*, 381:661-666 (1996).
Ellington, A.D., and J.W. Szostak. 1990. In vitro selection of RNA molecules that bind specific ligands. *Nature.* 346:818-22.
Forster, R., A. Schubel, D. Breitfeld, E. Kremmer, et al. 1999. CCR7 coordinates the primary immune response by establishing functional microenvironments in secondary lymphoid organs. *Cell.* 99:23-33.
* Horuk, Trends Pharm. Sci., 15:159-165 (1994).
* Jayasena, S.D. 1999. Aptamers: an emerging class of molecules that rival antibodies in diagnostics. *Clin Chem.* 45:1628-50.
* Jones, P.T., P.H. Dear, J. Foote, M.S. Neuberger, et al. 1986. Replacing the complementarity-determining regions in a human antibody with those from a mouse. *Nature.* 321:522-5.
Kledal, T.N., M.M. Rosenkilde, F. Coulin, G. Simmons, et al. 1997. A broad-spectrum chemokine antagonist encoded by Kaposi's sarcoma-associated herpesvirus. *Science.* 277:1656-9.
Klein, C., J.I. Paul, K. Sauve, M.M. Schmidt, et al. 1998. Identification of surrogate agonists for the human FPRL-1 receptor by autocrine selection in yeast. *Nat Biotechnol.* 16:1334-7.
Penfold, M.E., D.J. Dairaghi, G.M. Duke, N. Saederup, et al. 1999. Cytomegalovirus encodes a potent alpha chemokine. *Proc Natl Acad Sci U S A.* 96:9839-44.
* Riechmann, L., M. Clark, H. Waldmann, and G. Winter. 1988. Reshaping human antibodies for therapy. *Nature.* 332:323-7.
* Rossi, D., and A. Zlotnik. 2000. The Biology of Chemokines and their Receptors. *Annu. Rev. Immunol.* 18:217-242.
Tuerk, C., and L. Gold. 1990. Systematic evolution of ligands by exponential enrichment: RNA ligands to bacteriophage T4 DNA polymerase. *Science.* 249:505-10.
* Verhoeyen, M., C. Milstein, and G. Winter. 1988. Reshaping human antibodies: grafting an antilysozyme activity. *Science.* 239:1534-6.
Hesselgesser et al., J Biol Chem 1998, 273(25):15687-92.
Loetscher et al., "The Ligands of CXC Chemokine Receptor 3, I-TAC, Mig, and IP10, Are Natural Antagonists for CCR3*", J Biol Chem 2001, 276(5):2986-91.
Reckless J. and Grainger D.J., "Identification of Oligopeptide Sequences which Inhibit Migration Induced by a Wide Range of Chemokines," Biochem J. (1999) 340, pp. 803-811.
Ali, H., et al., "Chemoattractant Receptor Cross-desensitization," *The Journal of Biological Chemistry*, 274(10):6027-30 (1999).

*Primary Examiner*—Marianne P Allen
*Assistant Examiner*—Regina M DeBerry
(74) *Attorney, Agent, or Firm*—Brinks Hofer Gilson & Lione

(57) ABSTRACT

The present invention is directed to a modified cell migration assay allowing for improved identification and discrimination of chemokine receptor antagonists from non-specific migration blockers.

60 Claims, 14 Drawing Sheets

*MultiRAM using same cell population*

*MultiRAM using different cell population*

METHOD FOR MULTIPLE CHEMOKINE RECEPTOR SCREENING FOR ANTAGONISTS USING RAM ASSAY

RELATED APPLICATIONS

This application is a continuation-in-part of U.S. application Ser. No. 10/154,399, filed on May 22, 2002, now U.S. Pat. No. 7,282,338 which in turn claims priority to U.S. provisional application Ser. No. 60/296,682 filed Jun. 7, 2001. The disclosures of the priority applications are incorporated by references herein in their entireties.

FIELD OF THE INVENTION

The present invention is directed to an assay for identifying antagonists of chemoattractant receptors, such as chemokine receptors. One advantage of the assay compared with prior assays is its ability to discriminate valid chemoattractant receptor antagonists from those compounds that generate false positive and negative signals.

BACKGROUND

High-throughput screening (HTS) methods for identifying antagonists of chemoattractant receptors often rely on detecting perturbations in downstream events, such as cell migration. In the case of chemokine receptors, leukocyte cell migration is often assayed. However, compounds disrupting cell membranes or blocking downstream events mimic these outcomes, masquerading as candidate antagonists. Considerable efforts are then required to distinguish the genuine antagonists from those compounds or molecules that caused false positive signals. Identifying true antagonists, which represent only a small fraction of the large collections of candidate antagonists analyzed in high-throughput screens, is a formidable task. Realizing any savings in time or expense can bring a new drug to patients more quickly and less expensively.

Conventional assays that are adapted for use in HTS methods for screening small molecule antagonists of ligand-receptor interactions and signaling are usually one-dimensional. That is, they isolate and assay only the ligand-receptor interaction or the cellular signaling that ligand binding initiates, but not both. Because of this separation of physical interaction (ligand-receptor binding) from function (receptor signaling and downstream events), false positive signals are often observed, slowing discovery and development. False positives are molecules that give the desired result for undesirable reasons; they are often seen in screens for small molecule antagonists. Small molecules that initially appear to be inhibitors of receptor-ligand binding interactions (a desired result) may give such a result, for example, either by inhibiting the receptor-ligand interaction by binding the target receptor or ligand (desirable reasons), or by sickening or killing cells, or wielding other undefined effects (undesirable reasons).

Furthermore, conventional drug discovery formats for chemoattractant receptor antagonists fail to identify all clinically important molecules, a consequence of false negative signals. False negatives mean that clinically important molecules are undetected and remain undiscovered. For example, a conventional assay may identify a signal, as a result of binding of one or more molecules, i.e. a cluster of similar compounds. However, only the most potent molecule will be identified as a chemoattractant antagonist. As a consequence, a less potent molecule that permits chemoattractant receptor ligand-chemoattractant receptor binding, but inhibits chemoattractant receptor signaling, will be hidden in an initial screen for inhibitors of ligand binding.

One example of a conventional assay, the FLIPR® (Fluorometric Imaging Plate Reader) assay, illustrates these drawbacks. The FLIPR assay measures, over time, an intracellular mediator associated with activation of a cell bound receptor following exposure to a compound. Thus, FLIPR assays merely detect receptor-compound interactions that result in a change in the concentration of an intracellular mediator. The FLIPR assays may detect receptor-compound interactions that do not produce the downstream effect, some of which might also be considered false positives.

Chemokines, also known as "intercrines" and "SIS cytokines," comprise a family of more than 50 small secreted proteins (e.g., 70-100 amino acids and about 8-10 kiloDaltons) which attract, activate, and act as molecular beacons for the recruitment, activation, and directed migration of leukocytes and thereby aid in the stimulation and regulation of the immune system, flagging pathogens and tumor masses for destruction. The name "chemokine" is derived from chemotactic cytokine, and refers to the ability of these proteins to stimulate chemotaxis of leukocytes. Indeed, chemokines may comprise the main attractants for inflammatory cells into pathological tissues. See generally, Baggiolini et al., Annu. Rev. Immunol, 15: 675-705 (1997); and Baggiolini et al., Advances in Immunology, 55:97-179 (1994).

There are two classes of chemokines, CXC ($\alpha$) and CC ($\beta$), depending on whether the first two cysteines are separated by a single amino acid (C-X-C) or are adjacent (C-C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., Nature, 381: 661-666 (1996)).

The chemokines bind specific cell-surface receptors belonging to the family of G-protein-coupled seven-transmembrane-domain proteins (reviewed in Horuk, Trends Pharm. Sci., 15:159-165 (1994)), which are termed "chemokine receptors." On binding their cognate ligands, chemokine receptors transduce an intracellular signal though the associated trimeric G protein, resulting in a rapid increase in intracellular calcium concentration.

While defending the individual from invading pathogens and tumors, an improper regulation of the immune system can result in a disease state. Inappropriate chemokine signaling can either promote infections (Forster et al., 1999) or lead to diseases associated with defective chemokine signaling, including asthma, allergic diseases, multiple sclerosis, rheumatoid arthritis, atherosclerosis (reviewed in Rossi and Zlotnick, 2000), graft rejection, and AIDS. Moreover, recent work has shown that particular chemokines may have multiple effects on tumors including promoting growth, angiogenesis, metastasis, and suppression of the immune response to cancer, while other chemokines inhibit tumor mediated angiogenesis and promote anti-tumor immune responses. Because chemokines play pivotal roles in inflammation and lymphocyte development, the ability to specifically manipulate their activity will have enormous impact on ameliorating and halting diseases that currently have no satisfactory treatment. Chemokine receptor antagonists can be used to obviate the generalized and complicating effects of costly immunosuppressive pharmaceuticals in transplant rejection (reviewed in DeVries et al., 1999).

One aspect of chemokine physiology that makes these proteins and their receptors especially attractive therapeutic targets is their specificity. Unlike cytokines, which have pleiotropic effects, chemokines target specific leukocyte subsets and, in some settings, attract these cells without activating them. Thus, antagonism of a single chemokine ligand or receptor should have a relatively specific outcome.

To expedite the identification of chemoattractant receptor antagonists, such as those for chemokine receptors, an assay that weeds out false signals by testing both chemoattractant receptor binding and a biological function would hasten drug development.

SUMMARY OF THE INVENTION

In a first aspect, the invention provides methods for identifying a chemoattractant receptor antagonist. A cell having a chemoattractant receptor is incubated with a candidate antagonist in the presence of an excess of optimal ligand concentration for the chemoattractant receptor, and then cell migration is assayed. Cell migration indicates that the candidate antagonist is an antagonist.

In another aspect, the invention provides methods for identifying a chemokine receptor antagonist. A cell expressing a chemokine receptor is incubated with a candidate antagonist in the presence of an inhibitory concentration of chemokine ligand, and then cell migration is assayed. Cell migration indicates that the candidate antagonist is an antagonist.

In another aspect, the invention provides methods for identifying a chemokine receptor antagonist. A candidate antagonist of a chemokine receptor is first identified in a conventional assay. In a subsequent step, the candidate antagonist is incubated with a chemokine receptor bearing cell in the presence of inhibitory concentration of ligand, and then cell migration is assayed. Cell migration confirms that the candidate antagonist is an antagonist.

In another aspect, the invention provides a method for identifying a chemoattractant receptor antagonist. According to this method, a cell population including first and second chemoattractant receptors is contacted with an inhibitory concentration of a ligand for the first chemoattractant receptor, an inhibitory concentration of a ligand for the second chemoattractant receptor, and with a candidate antagonist. Next, the migration of the cell population is assayed, wherein migration identifies the candidate antagonist as an antagonist of at least one of the first and second chemoattractant receptors. Lastly, the determination whether an identified antagonist is an antagonist for one of the first and second chemoattractant receptors occurs.

In another aspect, the invention provides a method for identifying a chemoattractant receptor antagonist. According to this method, a first cell population and a second cell population, wherein the first cell population includes a first chemoattractant receptor, and wherein the second cell population includes a second chemoattractant receptor, are incubated and contacted with an inhibitory concentration of a ligand for the first and the second chemoattractant receptor and with a candidate antagonist. Next, the migration of the first and the second cell populations is assayed, wherein migration identifies the candidate antagonist as an antagonist of at least one of the first and second chemoattractant receptors. Last step includes determining whether an identified antagonist is an antagonist for one of the first and second chemoattractant receptors.

In yet another aspect, the invention provides for kits containing a cell migration apparatus and at least one chemokine.

These and other embodiments are discussed in detail below.

DETAILED DESCRIPTION OF THE INVENTION

Figure 1:
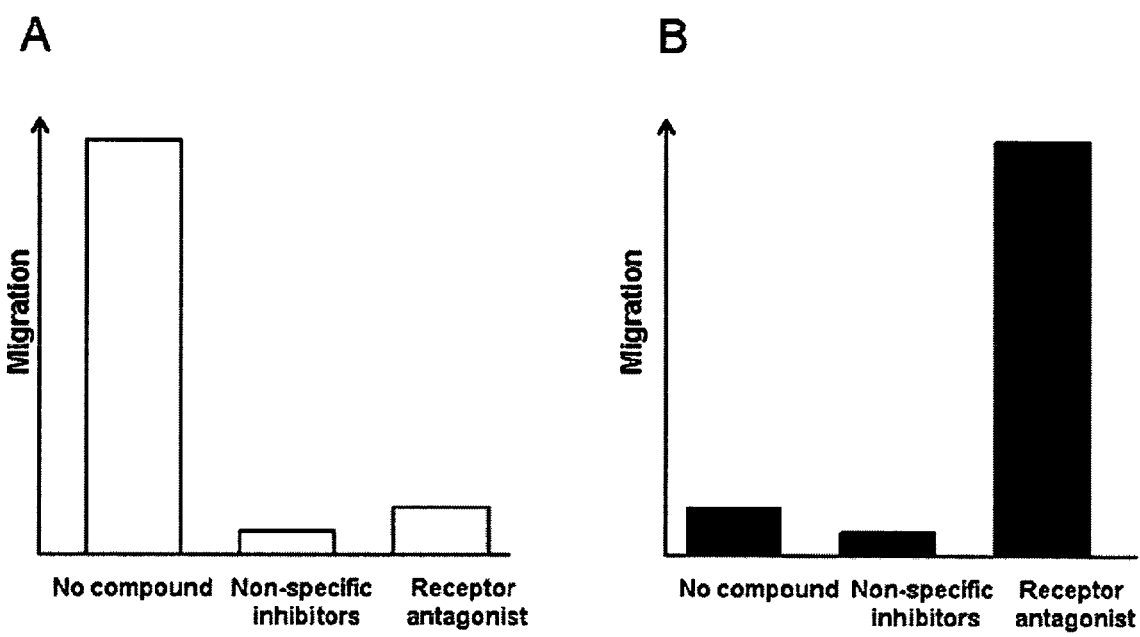
FIG. 1 shows graphs depicting the selective activation of cell migration by chemokine receptor antagonist by the (B) "reversed-activation of migration" (RAM) assay compared to (A) conventional assays.

The reversed-activation of migration, RAM, binary RAM (BiRAM), and MultiRAM screen assays of the invention identify and discriminate antagonists while significantly decreasing the prevalence of confounding false positive and negative signals found in other assays. The time and labor involved to confirm a potential pharmaceutical compound is therefore greatly reduced.

The methods of the RAM screen assay include:

(1) incubating a cell comprising a chemoattractant receptor, such as a chemokine receptor, with a candidate antagonist;

(2) contacting the cell with an inhibitory concentration of a ligand for the chemoattractant receptor; and (3) assaying cell migration.

The methods of the BiRAM and MultiRAM screen assays include:

(1) incubating a cell population comprising first and second chemoattractant receptors;

(2) contacting the cell population with an inhibitory concentration of a ligand for the first chemoattractant receptor;

(3) contacting the cell population with an inhibitory concentration of a ligand for the second chemoattractant receptor;

(4) contacting the cell population with a candidate antagonist;

(5) assaying migration of the cell population, wherein migration identifies the candidate antagonist as an antagonist of at least one of the first and second chemoattractant receptors; and (6) determining whether an identified antagonist is an antagonist for one of the first chemoattractant receptors, the second chemoattractant receptor, or both.

The methods of BiRAM and MultiRAM screen assays also include:

(1) incubating a first cell population and a second cell population, wherein the first cell population comprises a first chemoattractant receptor and wherein the second cell population comprises a second chemoattractant receptor;

(2) contacting the first and the second cell populations with an inhibitory concentration of a ligand for the first chemoattractant receptor;

(3) contacting the first and the second cell population with an inhibitory concentration of a ligand for the second chemoattractant receptor;

(4) contacting the first and the second cell populations with a candidate antagonist;

(5) assaying migration of the first and the second cell populations, wherein migration identifies the candidate antagonist as an antagonist of at least one of the first and second chemoattractant receptors; and (6) determining whether an identified antagonist is an antagonist for one of the first chemoattractant receptors, the second chemoattractant receptor, or both.

Cell migration is used to identify the candidate antagonist as an antagonist.

The method may further comprise a "pre-step" in which the concentration of a chemoattractant ligand (such as a chemokine) that inhibits cell migration is determined, the "inhibitory concentration" of a ligand for a chemoattractant receptor. Additional steps may be added, depending on the type of cell or agent being used, the assay, etc.

In one embodiment, the method may also comprise "post-step" in which the potencies of the antagonists that induced cell migration, as identified in the RAM, BiRAM, and MultiRAM screening assays, are determined.

While conventional screens for antagonists of cell migration measure the reduction of cell migration—a reduction in activity—RAM assays measure the activation of cell migration, an increase in activity (FIG. 1A, conventional migration assay; FIG. 1B, RAM assay). In the RAM assay, cells are challenged to migrate in the presence of migration-inhibitory concentrations of chemoattractants in response to a candidate antagonist; in a conventional assay, cells are challenged to migrate in response to a chemoattractant in the presence of a candidate antagonist. A compound that gives a false positive signal in a conventional cell migration assay (inhibiting migration) will fail to activate cell migration in the RAM format. In the RAM assay, only a true antagonist activates migration. This distinction allows for simple identification of authentic antagonists.

Another advantage of the RAM assay is that the identified antagonists are more likely to be therapeutically useful than those identified in conventional assays. A therapeutic chemoattractant receptor antagonist is specific for that receptor, exerting its effect through the receptor. Such an antagonist reduces the effective affinity between the chemoattractant and the receptor without compromising the physical integrity of the cell or completely disrupting the downstream signaling events leading to migration. A false positive identified in a conventional assay lacks at least one of these characteristics.

Figure 2:
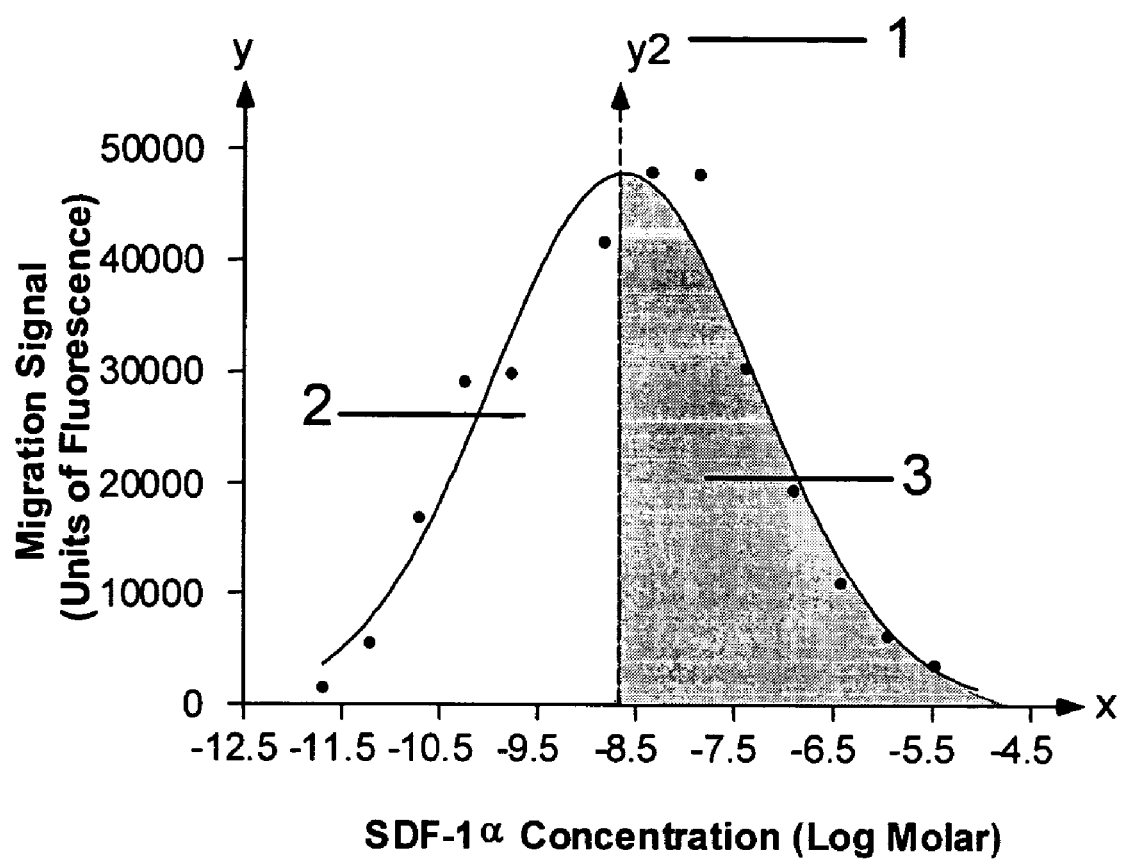
FIG. 2 shows a graph depicting the dose response curve for CXCR4 chemokine receptor-SDF-1α ligand interaction, relating to cell migration. X-axis, chemokine concentration (expressed as log); Y-axis, cell migration as measured in a cell migration assay (expressed as units of fluorescence).
Figure 3:
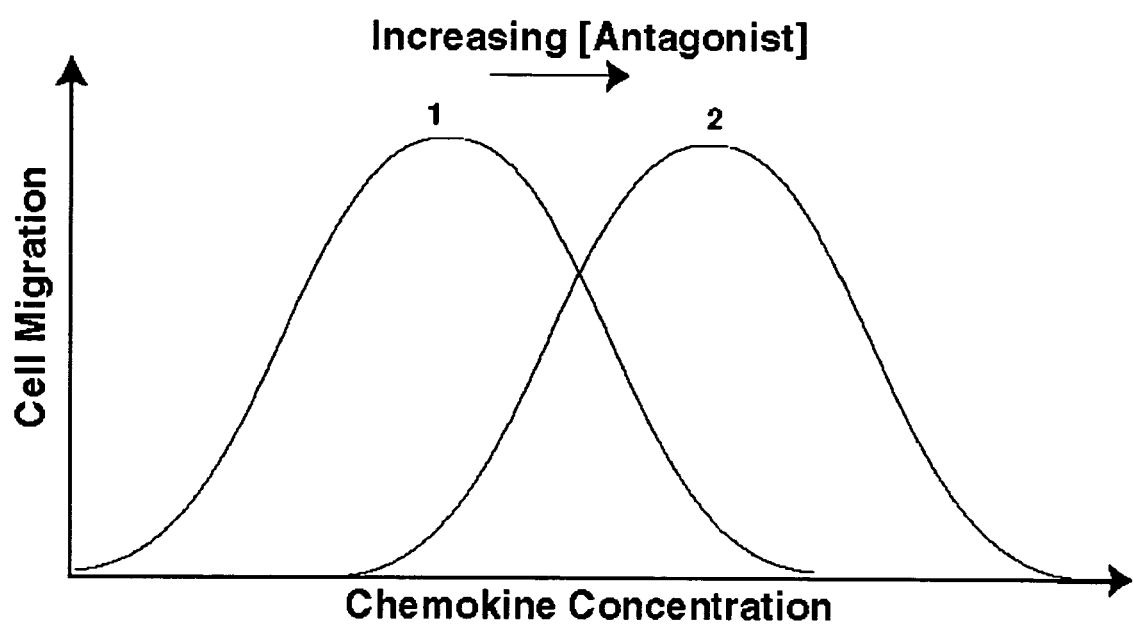
FIG. 3 shows a graph depicting representative curves that demonstrate the right-shift of the migration curve in the presence of an antagonist under RAM conditions. X-axis, chemokine concentration (expressed as log); Y-axis, cell migration as measured in a cell migration assay (numbers of cells).

One possible explanation for the success of the RAM assay is based on the observation that for a cell to migrate, the cell must have front end-back end polarity. Such polarity is often initiated by extracellular signals, such as chemokines. For cell migration, this polarity is achieved by a differential degree of chemoattractant receptor occupancy at the two ends of the cell. However, high concentrations of chemoattractant inhibit migration because all receptors are occupied in all directions of the cell; the cell lacks a directional cue. If increasing concentrations of ligand are plotted in relation to cell migration, a bell-shape curve is observed (an example is shown in FIG. 2). A receptor antagonist that reduces the effective affinity of a chemoattractant for a receptor allows the ligand to behave like a ligand with lower affinity. The bell-shape curve, first observed in the absence of antagonists, shifts to the right in the presence of increasing concentrations of antagonist (see e.g., FIG. 3). This is one possible explanation for the success of the present invention.

In addition, BiRAM and MultiRAM screening assays provide further advantages over conventional assays as well as the RAM screening assay. BiRAM and MultiRAM provide for significantly reduced screening time and cost of the screening as in these assays more then one receptor can be assayed simultaneously.

The inventors do not intend to be limited by this proposal.

Definitions of Terms

"RAM" means the reversed-activation of migration. Because RAM assays measure changes associated with interactions between cell-bound receptors and compounds of interest, RAM assays also measure a downstream effect of receptor activation—cell migration. Thus, RAM assays detect receptor-compound interactions that produce the downstream effect. In a "Binary RAM (BiRAM)" screen assay two types of chemoattractant receptor are assayed in the same assay. In a "MultiRAM" screen assay multiple types of chemoattractant receptors are assayed in the same assay.

The "cell migration assay" refers to an assay that tests the capacity of a cell to migrate in response to a signal. The cell migration assay can be used to identify the candidate antagonists as antagonists.

A "cell migration apparatus" refers to any conventionally used and available apparatus, for example the ChemoTx® system (NeuroProbe, Rockville, Md.) or any other suitable device or system (Bacon et al., 1988; Penfold et al., 1999) may be used. In one embodiment the cell migration apparatus may involve a two chamber cell migration apparatus format. However, any type of cell migration apparatus format may be used in RAM, BiRAM and MultiRAM, including for example, other plate-based, microscope-based, and those using digital video time-lapse microscopy formats. There are a variety of 'transwell' or 'Boyden-type' chamber assays in 24, 96 or even 384 well HTS plate-based formats. Neuro-Probe 96 well is an example only and is clearly not the only method. Also, a time lapse digital video microscopy where 'population' statistics for cell migration are gathered by analysis of the motility if single cells may be involved to measure cell migration according to the RAM, BiRAM, and MultiRAM methods of this invention. Furthermore, the term "cell migration apparatus" includes several microscope-based cell analysis systems available commercially to the pharmaceutical industry.

An "inhibitory concentration" of a chemoattractant is defined as the minimum chemoattractant concentration in excess of optimum concentration, which exerts a cell migration inhibition. This concentration is greater than one that activates cell migration. For example, an inhibitory concentration of chemoattractant can be one that causes greater than about 50%, preferably greater than 65%, more preferably greater than 80% cell migration inhibition. In one embodiment, an inhibitory concentration is also referred to as the "RAM concentration," which is an inhibitory chemokine concentration that exerts a complete (100%) cell migration inhibition. The amount of candidate antagonist that is present in the assay may vary, particularly depending on the nature of the candidate antagonist. The amount of any particular antagonist to include in a given assay can be readily determined empirically using methods known to those of skill in the art.

A "chemoattractant receptor" refers to a receptor that upon binding to a ligand induces cell migration. For example, a chemokine receptor is an example of a chemoattractant receptor.

The term "ligand" refers to a molecule that binds to a complementary receptor on a cell surface, and upon binding induces cell migration.

An "agonist" is a molecule, compound, or drug that binds to physiological receptors and mimics the effect of the endogenous regulatory compounds. An agonist could be any molecule that mimics a biological activity of endogenous molecule, such as a chemokine.

An "antagonist" refers to any molecule that binds to a receptor and does not mimic, but interferes with, the function of the endogenous agonist. Such compounds are themselves devoid of intrinsic regulatory activity, but produce effects by inhibiting the action of an agonist (e.g. by competing for an agonist binding sites). Therefore, an antagonist is any molecule that partially or fully blocks, inhibits, or neutralizes a biological activity, such as cell migration. The term "candidate antagonist," refers to a single antagonist to be determined in the RAM assays or multiple antagonists to be determined in the RAM assays.

The term "cell migration" refers to a type of biological activity due to intrinsic or extrinsic cell stimulation; motile response of a cell. For example, a candidate antagonist is a chemoattractant receptor antagonist if it induced an increase in cell migration in the presence of an inhibitory concentration of chemoattractant.

The "maximal ligand-activated cell migration" refers to the maximum number of cells that migrate into a lower chamber of the cell migration apparatus as a result of treatment with a chemokine receptor ligand.

The term "potency" refers to capacity of a molecule to produce strong physiological or chemical effects.

In the following sections, the RAM, BiRAM, and MultiRAM screening assays are illustrated using chemokines and chemokine receptors. However, any chemoattractant and chemoattractant receptor that induces cell migration may be used. Table A shows some examples of known chemoattractant receptors and some of their ligands.

TABLE A

Exemplary human chemoattractant receptors and exemplary ligands[1]

| Receptor | Examples of ligands[2] |
|---|---|
| BLT1 | Leukotriene B4 |
| PDGFR | Platelet-Derived Growth Factor |
| FPR | fMLP |
| FPRL1 | Unknown |
| CRTH2 | prostaglandin D2 |
| C3aR | C3a |
| C5aR | C5a |
| Noci-R | Nociceptin |
| EDG family | Sphingosine 1-phosphate |
| CB1 | Cannabinoids |
| VEGFR | Vascular endothelial growth factor |
| EGFR | Epidermal growth factor |
| FGFR | Fibroblast growth factor |
| P2Y receptor | P2Y |
| CTR | Calcitonin |
| CRLR | Calcitonin gene-related peptide (CGRP) |
| Histamine receptor | Histamine |
| Thrombin receptor | Thrombin |
| TrkB | Brain-derived neurotrophic factor (BDNF) |
| $TxA_2$ (TP) | Thromboxane $A_2$ ($TxA_2$) |
| $PGI_2$ (IP) | Prostacycline ($PGI_2$) |

[1]This list of chemoattractant receptors is not meant to be exhaustive.
[2]Only examples of some ligands for each receptor are given.
This list is not meant to be exhaustive.

A variety of different candidate antagonists may be screened using the subject methods. In one embodiment, a single candidate antagonist is screened. In another embodiment, multiple antagonists are screened simultaneously in the same assay according to the RAM, BiRAM, and MultiRAM methods of this invention.

Candidate antagonists encompass numerous chemical classes. In certain embodiments, they are organic molecules, preferably small organic compounds having a molecular weight of more than 50 and less than about 2,500 daltons. Candidate antagonists comprise functional groups necessary for structural interaction with proteins, particularly hydrogen bonding, and typically include at least an amine, carbonyl, hydroxyl or carboxyl group, preferably at least two of the functional chemical groups. The candidate antagonists often comprise cyclical carbon or heterocyclic structures and/or aromatic or polyaromatic structures substituted with one or more of the above functional groups. Candidate antagonists are also found among biomolecules including peptides, saccharides, fatty acids, steroids, purines, pyrimidines, derivatives, structural analogs or combinations thereof. Candidate antagonists of interest also include peptide and protein agents, such as antibodies or binding fragments or mimetics thereof, e.g., Fv, F(ab')$_2$ and Fab.

Candidate antagonists are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

RAM Screening Assay

In the RAM assay, a chemokine-bearing cell is incubated with a candidate antagonist and then contacted with an inhibitory concentration of a ligand for the target chemokine receptor. The ability of the cell to migrate is then assayed. If the cell migrates in the presence of a candidate antagonist in the RAM assay, then a positive signal has been observed. "Antagonist" includes any molecule that partially or fully blocks, inhibits, or neutralizes a biological activity, such as cell migration. Similarly, "agonist" includes any molecule that mimics a biological activity of molecule, such as a chemokine. Molecules that can act as agonists or antagonists include small organic molecules, macromolecules, antibodies or antibody fragments, fragments or variants of chemokines, peptides, etc. A "candidate antagonist" is a compound that is being tested for antagonist activity; likewise, a "candidate agonist" is a compound that is being tested for agonist activity.

Any cell migration assay format may be used, such as the ChemoTx® system (NeuroProbe, Rockville, Md.) or any other suitable device or system (Bacon et al., 1988; Penfold et al., 1999). In brief, these cell migration assays work as follows. After harvesting and preparing the cells bearing the active target chemokine receptor, the cells are mixed with candidate antagonists. The mixture is placed into the upper chamber of the cell migration apparatus. To the lower chamber, an inhibitory concentration of chemokine ligand is added. The migration assay is then executed, terminated, and cell migration assessed.

Figure 4:
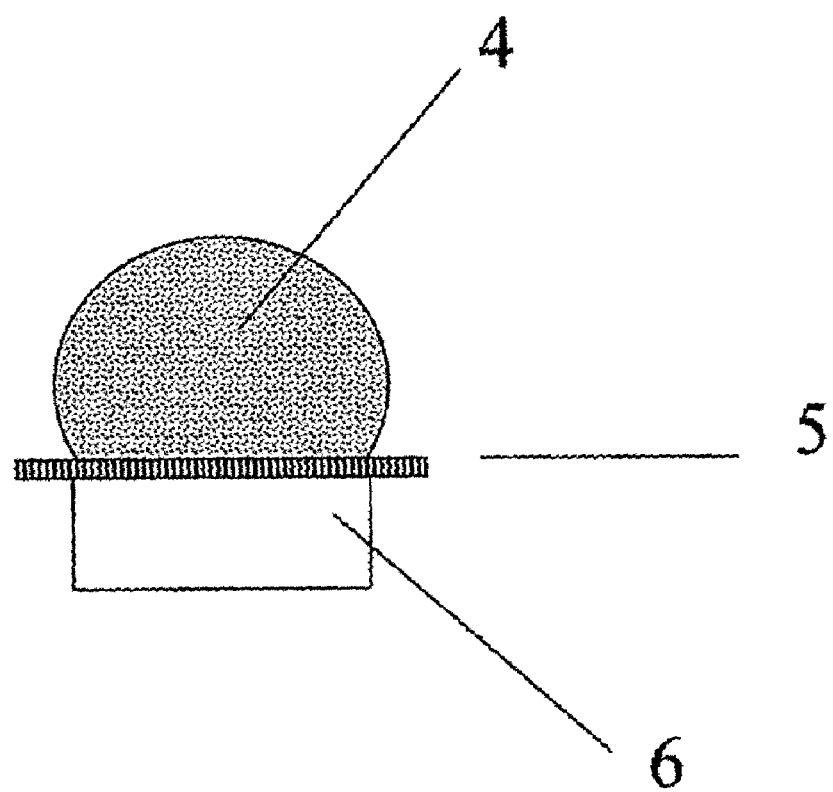
FIG. 4 depicts a schematic of a conventional cell migration assay.

To start the RAM assay, the solution of the inhibitory concentration of chemokine ligand is added to the lower chamber (6, FIG. 4) of a cell migration apparatus, and the cell suspension is placed into the upper chamber (4, FIG. 4) that is separated by a porous membrane (5, FIG. 4). The cells are incubated under culture conditions (37° C. for human cells) for 60 to 180 minutes in a humidified tissue culture incubator. The incubation period depends on the cell type and if necessary, can be determined empirically.

At the end of the incubation period, the assay is terminated. For example, non-migrating cells on the upper chamber of the apparatus are removed, using a rubber scraper or other manual method; enzymatically or chemically, e.g., EDTA and EGTA solutions. The membrane (5, FIG. 4) that separates the two chambers is then removed from the apparatus and rinsed with Dulbecco's phosphate buffered saline (DPBS) or water. The number of cells that migrate into the lower chamber is then determined.

The concentration of candidate antagonist to be screened in RAM assays may range from sub-nanomolar to millimolar. Screening a collection of small molecule compounds (such as a library synthesized by combinatorial chemistry), the concentration of candidate antagonists is typically about 1-20 µM. "Compound" includes small inorganic and organic molecules, macromolecules, peptides, proteins, polypeptides, nucleic acids, and antibodies.

BiRAM Screening Assay

Figure 8:
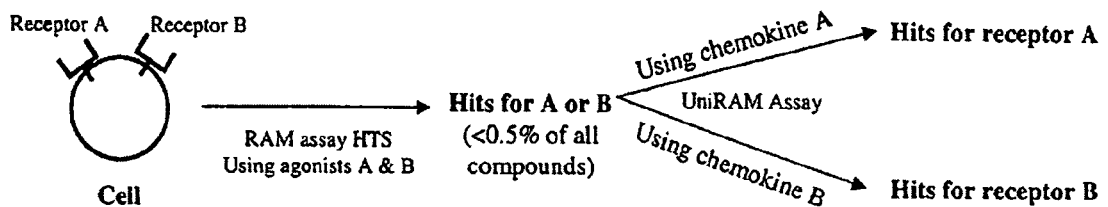
FIG. 8 is a schematic of a MultiRAM screening assay using the same cell population with multiple chemokine receptors on the cell surface.
Figure 9:
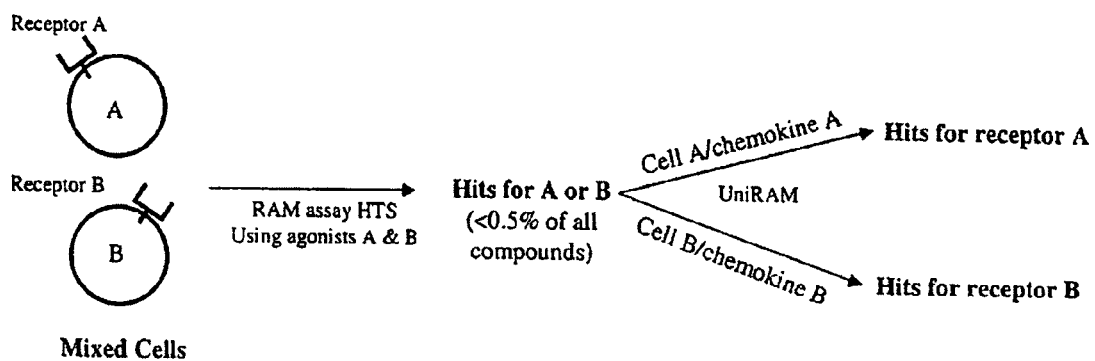
FIG. 9 is a schematic of a MultiRAM screening using multiple cell populations with different chemokine receptor each.

In the BiRAM screening assay, either a single cell population bearing two different chemokine receptors or two cell populations bearing a different type of chemokine receptor each, are incubated with a candidate antagonist and then contacted with an inhibitory concentration of ligands for the target chemokine receptors (FIG. 8 and FIG. 9). Next, the ability of the cell populations to migrate in response to the treatment with a candidate antagonist is assayed. If the cell migrated in the presence of a candidate antagonist in the BiRAM assay, then a positive signal is observed. As previously defined, an antagonist may be any molecule that partially or fully blocks, inhibits, or neutralizes a biological activity, for example cell migration. An agonist, on the other hand, may include any molecule that mimics a specific biological activity of an endogenous molecule, such as chemokine. These molecules that act as either agonists or antagonists include small organic molecules, macromolecules, antibodies or antibody fragments, fragments of variants of chemokines, peptides, etc. A "candidate agonist" is a compound that is being tested for agonist activity. A "candidate antagonist" is a compound that is being tested for antagonist activity.

Any cell migration format may be used, including for example, the ChemoTx® system (NeuroProbe, Rockville, Md.) or any other suitable device or system (Bacon et al., 1988; Penfold et al., 1999). In the cell migration assay, following harvesting, cells bearing the active target chemokine receptors are prepared and then mixed with a candidate antagonist. The mixture is placed in the upper chamber of the cell migration apparatus. Next, inhibitory concentrations of the respective chemokine ligands are added to the lower chamber of the cell migrating apparatus. The migration assay is then executed, terminated, and cell migration assayed.

There are two ways to carry BiRAM screening. The first method uses a single cell population expressing two chemokine receptors. The second method uses a mixture of two cell populations, wherein each cell population expresses a single but different type of chemokine receptor of interest. The first method is illustrated in FIG. 8; the second method according to the invention is illustrated in FIG. 9.

According to the first method of the BIRAM screening assay, the inhibitory concentrations of ligands for each of the chemokine receptors expressed on the cell are determined. This is achieved by testing increasing concentrations of a ligand for each chemokine receptor to obtain an inhibition of migration of the cell population at a minimum concentration of the respective ligands. The chemokine receptors are selected so that there is no cross-desensitization to ensure that signaling and cell migration mediated by one receptor does not interfere with receptor signaling mediated by the second receptor. Chemokine-receptor pairs that do not interfere with their respective signaling mechanisms are selected for the BiRAM screening assay.

To start the BiRAM screening assay, the selected single cell population expressing two chemokine receptors, is contacted with a candidate antagonist and with a mixture of two chemokine ligands to corresponding chemokine receptors present on the cell surface, at their respective inhibitory concentrations. The mixture of the chemokine ligands is added to the lower chamber (6, FIG. 4) of the cell migration apparatus, and the cell suspension is placed in the upper chamber (4, FIG. 4) that is separated by a porous membrane (5, FIG. 4). The cells are incubated under culture conditions (37° C. for human cells) for 60 to 90 minutes in a humidified tissue culture incubator. The incubation period depends on the cell type and if necessary, can be determined empirically.

At the end of the incubation period the assay is terminated and the non-migrating cells are removed from the upper chamber of the cell migration apparatus, using a rubber scraper or other manual method, enzymatically or chemically, e.g., EDTA and EGTA solutions. The membrane (5, FIG. 4) that separates the two chambers is then removed from the apparatus and rinsed with Dulbecco's phosphate buffered saline (DPBS) or water. The number of the cells that migrate into the lower chamber as a result of the candidate antagonist treatment is then determined and considered to be a positive hit.

BiRAM screening identifies hits, which correspond to either of the chemokine receptors present on the population of cells used in the screening assay. Although the hits may identify an antagonist to one or more chemokine receptors, the identity of this chemokine receptor(s) reacting in the assay and causing cell migration is not known at this stage of the assay. However, because the hit rate is very low, i.e. less than 1%, receptors identity can be then determined by re-screening the candidate antagonist in a RAM assay in which only one chemokine is applied at a time. The RAM assay has been described in more detail above and in the U.S. application Ser. No. 10/154,399 filed on May 22, 2002, which is incorporated by reference in its entirety, except that in an event of any inconsistent disclosure or definition from the present application, the disclosure and definition herein shall prevail.

According to the second option of carrying out the BiRAM screening assay, the inhibitory concentrations of ligands for each of the chemokine receptors on the respective cell populations are determined as described previously for the first method. Referring to FIG. 9, this method uses a mixture of two cell populations each expressing a different chemokine of interest. Since in this case there is no cross-desensitization between different cell populations with different chemokine receptors, these chemokine receptors will not interfere with their respective signaling mechanisms.

Next, the BiRAM screening assay is carried out in the presence of a mixture of the chemokines all at their respective inhibitory concentrations. Hits are identified by a positive migration signal. Similarly to the first method, the receptor's identity for a given hit is further determined by a RAM screening where one cell population and one chemokine are used.

The concentration of candidate antagonist to be screened in BiRAM assays may range from sub-nanomolar to millimolar. Screening a collection of small molecule compounds (such as a library synthesized by combinatorial chemistry), the concentration of candidate antagonists is typically about 1-20 µM. "Compound" includes small inorganic and organic molecules, macromolecules, peptides, proteins, polypeptides, nucleic acids, and antibodies.

MultiRAM Screening Assay

In the MultiRAM screening assay, either a single cell population bearing multiple different chemokine receptors (i.e. 2, 3, 4, 5, etc. different receptors) or multiple cell populations bearing a different chemokine receptor each (i.e. 2, 3, 4, 5, etc. different cell populations), are incubated with a candidate antagonist and then contacted with an inhibitory concentration of ligands for the target chemokine receptors. The ability of the cell populations to migrate is then assayed. If the cell migrated in the presence of a candidate antagonist in the MultiRAM assay, then a positive signal is observed.

Similarly to BiRAM screening, there are also two ways to carry MultiRAM screening. However, in the MultiRAM, the first method uses a single cell population expressing multiple chemokine receptors and the second method uses a mixture of multiple cell populations, wherein each cell population expresses a single but different type of chemokine receptor of interest.

Once a cell population(s) to use in either method of the MultiRAM screen assay has been selected, the procedure to determine the antagonists of the chemokine receptors is followed as previously described for BiRAM screen assay.

In the BiRAM and MultiRAM screening, antagonism to one, two or multiple receptors may produce a positive migration signal. Therefore, in BiRAM and MultiRAM screening assays an increased number of candidate antagonists and corresponding chemoattractant receptors may be tested without the need to initially distinguish the activity of each chemoattractant receptor in response to its antagonist. Once hits are identified, a RAM assay is employed to directly identify the candidate antagonist. This results in a significantly reduction in the cost of screening of the candidate antagonists in addition to reduction in the overall screening time.

Cell Populations for Use in the RAM, BiRAM and MultiRAM Assays

Cells population expressing a target chemokine receptor (or chemoattractant receptor) or a cell population expressing more than one target chemokine receptors (or chemoattractant receptors) for use in the RAM, BiRAM and MultiRAM, respectively, may be gathered by a variety of methods, for example by centrifugation after collection from a subject or release from culture. The pelleted chemokine receptor cells are then resuspended in a buffer at an appropriate density, depending on cell type and cell size. Convenient cell concentrations range from about $1 \times 10^6$ to $1 \times 10^7$ cells/ml; often about $2.5 \times 10^6$ cells/ml is suitable.

Cells that can be assayed in all RAM screen formats include all those that express at least one chemoattractant receptor on the cell surface, such as human monocytes, or other cells engineered to express recombinant chemoattractant receptors and are competent to activate cell migration.

For example, three chemokine receptors CCR3, CCR4, and CCR8 are preferentially expressed by Th2 cells, mast cells or eosinophils and therefore represent therapeutic targets.

TABLE B

Exemplary cell types and exemplary cell receptors expressed on the surface of these cells.

| Exemplary cell types | Exemplary receptors |
| --- | --- |
| Monocyte | CCR2, CCR2, CXCR1/2, CXCR4, CCR12 (FPRL-1) |
| Neurophil | CXCR1, CXCR2, CCR12 (FPRL-1), CXCR4. C5aR |
| Lymphocyte | CCR2, CCR4, CCR5, CCR7, CCR8, CXCR4, CXCR4, CXCR5 |
| Dendritic cells | CCR1, CCR2, CCR5, CCR6, CCR7, CXCR1/2, CXCR4 |
| THP-1 | CCR1, CCR2, CXCR4, CXCR1/2 |
| MOLT-4 cells | CCR9, CXCR4 |

This list of cell types and chemoattractant receptors is not meant to be exhaustive.
This list is not meant to be exhaustive.

The Method of Determining Inhibitory Concentrations of Ligands

A dose response of cell migration to a chemokine ligand can be performed to define the inhibitory concentrations of a chemokine ligand. Any standard method for determining dose response curves can be used. One such method includes harvesting cells expressing the target chemokine receptor, adding the cells to a cell migration device in the presence of increasing amounts of chemokine, measuring cell migration, plotting cell migration versus chemokine concentration, and then calculating from the graph those chemokine concentrations that inhibit cell migration.

As an example, a conventional cell migration assay, such as the ChemoTx® system (NeuroProbe, Rockville, Md.) or any other suitable device or system (Bacon et al., 1988; Penfold et al., 1999) may be used. To obtain a dose response curve, cells expressing the target receptor are gathered. A chemokine ligand is prepared in a concentration series by serial dilution in a buffer. The concentration range is typically between 0.1 nM and 10 mM, but will vary with ligand.

To start the cell migration assay, solutions of the various chemokine ligand concentrations are added to the lower chamber (6, FIG. 4) of a cell migration apparatus, and the cell suspension is placed into the upper chamber (4, FIG. 4) that is separated by a porous membrane (5, FIG. 4). The cells are incubated under culture conditions (37° C. for human cells) for 60 to 180 minutes in a humidified tissue culture incubator. The incubation period depends on the cell type and if necessary, can be determined empirically.

At the end of the incubation period, the assay is terminated and the non-migrating cells are removed from the upper chamber of the cell migration apparatus, using a rubber scraper or other manual method; enzymatically or chemically, e.g., EDTA and EGTA solutions. The membrane (5, FIG. 4) that separates the two chambers is then removed from the apparatus and rinsed with Dulbecco's phosphate buffered saline (DPBS) or water. The number of cells that migrate into the lower chamber is then determined.

Cell migration (Y-axis) is then plotted against the log (chemokine concentration) (X-axis). This results in a bell-shaped curve (FIG. 2; see Examples). From this plot (FIG. 2), the lowest concentration of chemokine that inhibits cell migration can be determined. For ease of reference, a second Y-axis ($y_2$, 1, FIG. 2) can be drawn through the bell curve, intersecting at its apex (maximal cell migration) and the corresponding value on the X-axis. Those concentrations to the left of the $Y_2$-axis (lower) are stimulatory (2, FIG. 2); those to the right (higher) are inhibitory (3, shaded region, FIG. 2). These concentrations are the "inhibitory concentrations" for cell migration (chemotaxis). For example, to determine the concentration at with migration is inhibited by about 90% of the maximum (to the right of the $Y_2$-axis, the "inhibitory" concentrations), the value corresponding to about 10% of maximal cell migration on the Y-axis is located. If the maximal cell migration signal is, e.g., $3.5 \times 10^4$ cells, 10% thereof would be 350 ($3.5 \times 10^4 \times 0.1$). The inhibitory ligand concentration is then determined by locating the corresponding X-axis coordinate. Preferably, the level of inhibition is about 50%, 60%, 70% or 80% of maximal cell migration. More preferably, the level of inhibition is about 90% or even more preferably about 95% or 100% inhibition as compared to the maximal signal for migration. The determined chemokine concentration varies and depends on the nature of the receptor, the chemokine ligand and the target cell. Varying the degree of chemotactic inhibition can be used to modulate the sensitivity of the RAM as well as BiRAM and MultiRAM screening assays.

Application of RAM BiRAM and MultiRAM Assays in Comprehensive Screens for Therapeutic Antagonists RAM, BiRAM and MultiRAM screening assays can be performed in conjunction with any other assay used to screen for chemokine receptor antagonists. Not only is the RAM, BiRAM and MultiRAM formats useful as a primary HTS steps, but it also provide a confirmatory or secondary assay for candidate antagonists identified in other assays. For example, a HTS method that measures $Ca^{2+}$ mobilization, including those based on the FLIPR™ system (Molecular Devices Corp., Sunnyvale, Calif.) or other reporter-based methods which assay increases in free intracellular $Ca^{2+}$ levels, can be used as a primary assay. RAM, BiRAM and MultiRAM assays can be used to confirm such candidates, or vice-versa. As secondary assays, RAM, BiRAM and MultiRAM would discriminate those candidate antagonists that exert non-specific effects. When RAM, BiRAM and MultiRAM assays are used with other HTS methods, a means for discriminating true hits from non-specific blockers is provided.

The RAM, BiRAM and MultiRAM assays can be applied to any other assay format measuring cell migration or receptor activation, including methods that do not require migration of cells across a porous membrane. More useful technologies offering higher throughput and lower cost may be developed based on use of the RAM concept.

Chemokine Receptors and Ligands

Cells that can be assayed in the RAM, BiRAM and MultiRAM formats include all those that express at least one chemokine receptor on the cell surface, such as human monocytes, or other cells engineered to express recombinant chemokine receptors and are competent to activate cell migration. Known chemokine receptors and some of their ligands are shown in Table B. Examples of chemokine receptors include, but are not limited to, the CXC class, e.g., CXCR1, CXCR2, CXCR3, CXCR4, CXCR5; the CC class, CCR1, CCR2, CCR3, CCR4, CCR5, CCR6, CCR7, CCR8, CCR9, CCR10 and CCR11; the CX3CR class, such as CX3CR1 and the XCR class, such as XCR1.

An example of a non-chemokine chemoattractant receptor is C5aR; the ligand for which is C5a. Also see Table A for other examples.

TABLE C

Summary of the known chemokine receptors and some of their known human ligands (Rossi and Zlotnik, 2000)

| Receptor | Human ligands |
| --- | --- |
| CXCR1 | IL-8, GCP-2 |
| CXCR2 | IL-8, GCP-2, Gro α, Gro β, Gro γ, ENA-78, PBP |
| CXCR3 | MIG, IP-10, I-TAC |
| CXCR4 | SDF-1α/PBSF |
| CXCR5 | BLC/BCA-1 |
| CCR1 | MIP-1α, MIP-1β, RANTES, HCC-1, 2, 3, and 4 |
| CCR2 | MCP-1, MCP-2, MCP-3, MCP-4 |
| CCR3 | eotaxin-1, eotaxin-2, MCP-3 |
| CCR4 | TARC, MDC, MW-1α, RANTES |
| CCR5 | MIP-1α, MIP-1β, RANTES |
| CCR6 | MIP-3α/LARC |
| CCR7 | MIP-3β/ELC, 6Ckine/LC |
| CCR8 | I-309 |
| CCR9 | TECK |
| XCR1 | Lymphotactin |
| CX3CR1 | Fractalkine/neurotactin |
| CXCR6 | CXCL16 |
| CCR10 | CTACK |

Chemokines that can be used in the RAM assay include all known chemokines. Examples of chemokines include, but are not limited to, IL-8, GCP-2, Gro α, Gro β, Gro γ, ENA-78, PBP, MIG, IP-10, I-TAC, SDF-1α (PBSF), BLC (BCA-1), MIP-1α, MIP-1β, RANTES, HCC-1, -2, -3, and -4, MCP-1, -2, -3, and -4, eotaxin-1, eotaxin-2, TARC, MDC, MIP-3α (LARC), MIP-3β (ELC), 6Ckine (LC), I-309, TECK, lymphotactin, fractalkine (neurotactin), TCA-4, Exodus-2, Exodus-3 and CKβ-11.

Chemokine receptor/ligand combinations include those associated with inflammatory disorders, infectious diseases and transplant rejection. Such combinations include CX3CR1/fractalkine (transplantation), CCR5/MIP-1α, MIP-1β, or RANTES (HIV), CXCR4/SDF-1α (HIV); and CCR7/MIP-3β, ELC or 6Ckine LC (inflammatory or allergic diseases, e.g. asthma, multiple sclerosis, etc.).

In the BiRAM and MultiRAM screening assays using a single cell population comprising either two or multiple different receptors, respectively, the chemokine receptors must be pre-selected to ensure the lack of cross-desensitization. It is important to recognize that receptors not only initiate regulation of physiological and biochemical function but also are themselves subject to many regulatory and homeostatic controls. For example, continued stimulation of cells with agonists generally results in a state of desensitization (also referred to as refractoriness or down regulation), such that the effect that follows continued or subsequent exposure to the same concentration of drug is diminished. Thus, the chemokine receptors for use in the BiRAM and MultiRAM screening assay with a single cell population bearing two or multiple receptors, respectively, are selected to avoid cross-desensitization. In other words, the chemokine receptors are selected so that they do not act on a single signaling pathway to ensure that a continuous stimulation by one ligand does not diminish effectiveness of a receptor stimulated by another ligand.

Candidate Antagonists

Any molecule or compound can be screened for chemokine receptor antagonist activity. Compounds that inhibit chemokine receptor/ligand activities, such as activating cell migration or modulating intracellular $Ca^{2+}$ concentrations are candidate antagonists.

Such molecules that may exert such antagonistic effects include small molecules that bind to chemokine receptors or their ligands. Examples of small molecule antagonists include small peptides, peptide-like molecules, preferably soluble and synthetic non-peptidyl organic or inorganic compounds. Other potential antagonist molecules include nucleic acids such as aptamers and antibodies. These molecules may be collected into various libraries can be quickly screened for novel chemokine receptor antagonists using the RAM, BiRAM or MultiRAM assays.

Almost any antibody (Ab) that inhibits chemotactic cell migration is also a candidate antagonist. Examples of antibody antagonists include polyclonal, monoclonal, single-chain, anti-idiotypic, chimeric Abs, or humanized versions of such Abs or fragments. Abs may be from any species in which an immune response can be raised. Humanized Abs are exceptionally well-adapted for treatment of diseases and represent attractive candidate antagonists (Jones et al., 1986; Riechmann et al., 1988; Verhoeyen et al., 1988); (U.S. Pat. No. 4,816,567, 1989). Such antibodies may bind to chemokine receptors to inhibit cell migration.

Alternatively, a potential antagonist or agonist may be a closely related protein, for example, a mutated form of a chemokine receptor ligand or other protein that recognizes a chemokine receptor interacting protein, but imparts no effect, thereby competitively inhibiting chemokine receptor action.

Aptamers are short oligonucleotide sequences that can be used to recognize and specifically bind almost any molecule, such molecules may also act antagonistically. The systematic evolution of ligands by exponential enrichment (SELEX) process (Ausubel et al., 1987; Ellington and Szostak, 1990; Tuerk and Gold, 1990) is powerful and can be used to find such aptamers. Aptamers have many diagnostic and clinical uses, including as antagonists. In addition, they are inexpensive to manufacture and can be easily applied in a variety of formats, including administration in pharmaceutical compositions, bioassays, and diagnostic tests (Jayasena, 1999). The RAM, BiRAM and MultiRAM assays can also be used as screens to isolate aptamers de novo.

Quantifying Migratory Cells

Quantifying migratory cells may be accomplished by a large variety of available methods, such as those that assay the amount of DNA, (e.g., the CyQuant Cell Proliferation Kit (Molecular Probes)) and then assaying the generated signal, such as fluorescence. Other methods include counting the cells using a microscope, or labeling cells with a suitable detectable marker, such as dyes (such as Calcein AM (NeuroProbe) or the many labels available from Molecular Probes (Eugene, Oreg.)) or radioactive labeling (e.g. cell surface iodination with $^{135}$I, protein synthesis labeling with $^{35}$S-methionine/$^{35}$S-cysteine or nucleic acid labeling with $^{3}$H).

Buffers and Cell Culture Media

Buffers that may be used to prepare the various solutions include cell culture media, although serum or other growth and chemotactic factors may be removed so that the results in a cell migration assay are not confounded and can be mostly attributable to the chemokine-chemokine receptor interaction. In some cases, a protein may be added to support the cells, such as various albumins, including bovine serum albumin. Optimal media selection depends on the cell type; that media used to culture the cells usually represents a preferred option. Examples of suitable culture media include Iscove's Modified Dulbecco's Medium (IMDM), Dulbecco's Modified Eagle's Medium (DMEM), Minimal Essential Medium Eagle (MEM), Basal Medium Eagle (BME), Click's Medium, L-15 Medium Leibovitz, McCoy's 5A Medium, Glasgow Minimum Essential Medium (GMEM), NCTC 109 Medium, Williams' Medium E, RPMI-1640, and Medium 199. A medium specifically developed for a particular cell type/line or cell function, e.g. Madin-Darby Bovine Kidney Growth Medium, Madin-Darby Bovine Kidney Maintenance Medium, various hybridoma media, Endothelial Basal Medium, Fibroblast Basal Medium, Keratinocyte Basal Medium, and Melanocyte Basal Medium are also useful. If desired, a protein-reduced or free and/or serum free medium and/or chemically defined, animal component free medium may be used, e.g., CHO, Gene Therapy Medium or QBSF Serum-free Medium (Sigma Chemical Co.; St. Louis, Mo.), DMEM Nutrient Mixture F-12 Ham, MCDB(105, 110,131, 151,153,201 and 302), NCTC 135, Ultra DOMA PF or HL-1 (both from Biowhittaker; Walkersville, Md.), may be used.

If desired, the media may be further supplemented with reagents that limit acidosis of the cultures, such as buffer addition to the medium (such as N,N-bis(2-hydroxyethyl)-2-aminoethanesulfonic acid (BES), bis(2-hydroxyethyl) amino-tris(hydroxymethyl)methane (BIS-Tris), N-(2-hydroxyethyl)piperazine-N'3-propanesulfonic acid (EPPS or HEPPS), glyclclycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminomethane (Tris), etc.). Frequent medium changes and changes in the supplied $CO_2$ (often approximately 5%) concentration may also be used to control acidosis.

Kits

Components to carry out RAM, BiRAM and MultiRAM screening assays may be assembled into kits, containers, packs, or dispensers together with instructions for administration. When supplied as a kit, the different components of the composition may be packaged in separate containers and admixed immediately before use. Such packaging of the components separately may permit long-term storage without losing the active components' functions. For example, a kit may include a cell migration apparatus, a chemokine receptor-bearing cell and at least one chemokine for the chemokine receptor bearing cell. The chemokine may be supplied lyophilized or in solution.

(a) Containers or Vessels

The reagents included in the kits can be supplied in containers of any sort such that the life of the different components are preserved, and are not adsorbed or altered by the materials of the container. For example, sealed glass ampules may contain lyophilized chemokine or a buffer that has been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix; for example, lyophilized chemokine in one compartment, and a buffer or water in the other. Removable membranes may be glass, plastic, rubber, etc.

(b) Instructional Materials

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

EXAMPLES

The following examples are intended to illustrate and validate the RAM, BiRAM and MultiRAM assay concept of the present invention without limitation. The chemoattractant receptor and ligands used to illustrate the invention are chemokine receptors and chemokines. However, any chemoattractant ligand for any chemoattractant receptor may be used. For examples, see Table A.

Examples 1, 2 and 4 demonstrate the effectiveness of the RAM assay, testing specific and non-specific antagonists of CXCR4 as discovered in conventional assays. Example 3 demonstrates the broad applicability of chemoattractant receptors by examining three chemokine receptors.

CCR1 and CCR2 ligands, MIP-1α and MCP-1, respectively, were purchased from PeproTech: MIP-1α lot#: 090235 and MCP-1 lot#: 020231.

Example 1

Determining Inhibitory Concentration of SDF-1α (CXCR4)

To obtain a dose response curve for activated lymphocytes expressing cell surface CXCR4, a conventional cell migration assay was used (Bacon et al., 1988; Penfold et al., 1999). The activated lymphocytes were prepared by culturing lymphocytes in the presence of interleukin-2 (IL-2) and phytohemeagglutinin (PHA). To isolate peripheral blood lymphocytes (i.e., a thin layer of white blood cells called the buffy coat), blood samples from the Stanford blood center were centrifuged for 10 minutes at 1200 rpm leaving a concentrated fraction containing predominantly white blood cellular fraction. Next, peripheral blood mononuclear cells (PBMC) were prepared by the standard Ficoll-Pague (Amersham Biosciences) gradient centrifugation method. Following the centrifugation, PBMC were removed and resuspended in MACS (Dulbecco's Phosphate Buffered Saline, DPBS; 1% Bovine Serum Albumin, BSA) buffer. After removal of the PMBCs, the monocytes were separated by a CD14 positive selection column mounted on an AutoMac (Multenyi Biotech). The monocyte-free lymphocytes were then cultured in RPMI cell culture medium (supplemented with 10% Fetal Bovine Serum (FBS), 1% L-Glutamine (2.9 mM), 1% Pen/Strep (100 ug/ml), and IL-2 (0.01 ug/ml). Next, PHA was added to each culture flask of lymphocyte preparation for a final concentration of 2.5 ug/ml. Cells were left in culture media for 3 days and following this incubation period the cells were harvested by centrifugation and then resuspended in cell migration buffer (Hank's balanced salt solution (HBSS)/0.1% bovine serum albumin (BSA) at $2.5 \times 10^6$ cells/ml. These cells were then used in the cell migration assay.

The CXCR4 ligand stromal-derived factor (SDF-1α) was prepared in a concentration series (0.1 nM to 10 mM) by serial dilution in cell migration buffer. At low concentrations, SDF-1α activates cell migration of CXCR4-bearing activated lymphocytes. SDF-1α ligand was loaded in the bottom chamber of a ChemoTx® cell migration apparatus (5 μm pore polycarbonate polyvinylpyrrolidone-coated filters (Neuroprobe; Gaithersburg, Md.); 29 μl/well) and 20 μl of cell suspension was placed in the upper chamber. The cells were incubated at 37° C. for 150 minutes. The assay was terminated by removing the cells from the upper chamber and membrane surface using a rubber scraper. The cells that migrated to the lower chamber were quantified by the CyQuant assay (Molecular Probes; Eugene, Oreg.), a fluorescent dye method that measures nucleic acid content.

To determine the minimum concentration of SDF-1α to inhibit cell migration, chemokine concentration (X-axis) is plotted against relative fluorescent units (RFUs), correlating to the number of cells migrating (Y-axis) (FIG. 2). Initially as SDF-1α concentration increases, cell migration increases linearly (2, FIG. 2); however, at higher concentrations (3, FIG. 2), migration levels first flatten and then decrease until migration is barely detectable. This bell-shaped curve is typical of chemokine and chemokine receptor-mediated cell migration. In this experiment, 1 μM of SDF-1α was determined to be completely inhibitory; the inhibitory concentration range was 200 nM to 1 μM.

Example 2

Validation of the RAM Assay Using a Viral Polypeptide Antagonist of CXCR4

In the RAM assay, antagonists of chemokine receptors are identified by their ability to activate migration of cells that are incubated with inhibitory chemokine concentrations. To validate the RAM assay, the viral chemokine, vMIP-II, was used as a CXCR4 antagonist. vMIP-II binds with high affinity to CXCR4, blocking receptor signaling and inhibiting cell migration, competing with CXCR4's usual ligand, SDF-1α (Kledal et al., 1997). If CXCR4 expressing cells that are immobilized by inhibitory concentrations of SDF-1α are activated to migrate in the presence of vMIP-II with increased migration, this result would verify the RAM assay principle. For reference and as a control, a conventional cell migration assay was performed. In the conventional assay format, cell migration is inhibited by vMIP-II.

Cell migration was measured using the two formats with the corresponding amounts of SDF-1α chemokine:

(1) a conventional assay (control); 1 nM SDF-1α; and
(2) a RAM assay, 1 μM SDF-1α.

Activated lymphocytes expressing cell surface CXCR4 were harvested as in Example 1. For the conventional assay, a concentration series of vMIP-II was first mixed with activated lymphocytes, and the solution then placed in the upper chamber of a ChemoTx® cell migration apparatus (5 μm pore polycarbonate polyvinylpyrrolidone-coated filters (Neuroprobe), 20 μl/well); 29 μl of a 1 nM solution of SDF-1α was placed in the lower chamber. For the RAM assay, the cells were prepared as for the conventional assay, except the SDF-1α concentration in the lower chamber was 1 μM. The cells were incubated at 37° C. for 150 minutes. The assay was terminated by removing the cells from the upper chamber and membrane surface using a rubber scraper. The cells that migrated to the lower chamber were quantified by the CyQuant assay (Molecular Probes).

In the conventional assay (FIG. 5A), cell migration was partially inhibited at 11 nM of vMIP-II; cell migration was further inhibited as the vMIP-II concentration increased (up to 100 nM), verifying that vMIP-II is an antagonist of CXCR4. In the RAM assay format (FIG. 5B), little migration was observed in the absence of vMIP-II. However, migration was activated in the presence of vMIP-II at 11 nM, mirroring the decrease of migration seen in the conventional assay (FIG. 5A). Increased vMIP-II concentration correlated with an increase in cell migration, with maximal migration being observed at 100 nM.

Example 3

Validation of RAM Assay Using Known Small Molecule Antagonists of CXCR3, CXCR4 and CCR1

RAM assays were performed as described in Example 2, except previously identified small molecule antagonists instead of vMIP-II were used, as well as additional cell types as described in Table 1.

TABLE 1

| | Experimental variables | | |
|---|---|---|---|
| Antagonist[1] | Receptor | Ligand(s) | Cells |
| RAMAG-1 | CXCR3 | 1-TAC (250 nM), IP-10 | activated human lymphocytes |
| RAMAG-2 | CXCR4 | SDF-1α | CXCR4-expressing MOLT-4 cells (human T lymphoblast; American Type Tissue Collection (ATCC); Manassas, VA) |
| RAMAG-3 | CCR1 | MIP-1α | THP-1 cells (human monocytic; ATCC) |

[1]As defined using a conventional cell migration assay and further independently confirmed.
[2]Inhibitory concentrations determined as in Example 1.

Figure 6:
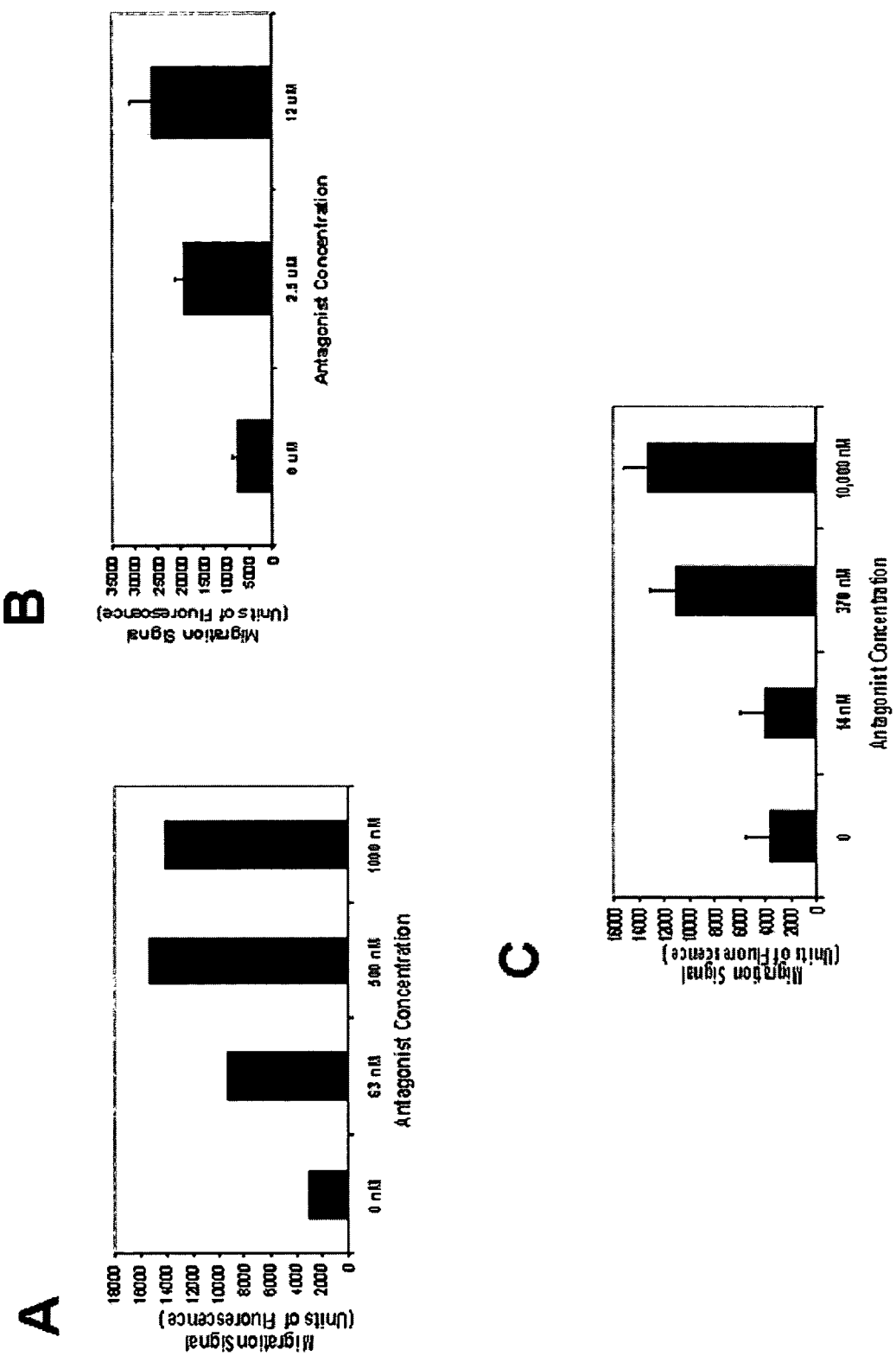
FIG. 6 shows bar graphs depicting the results from a RAM assay validation experiment using small organic CXCR4 antagonists. Chemokine SDF-1α-mediated cell migration in the presence of small organic molecule CXCR4 antagonist (A) RAMAG-1, (B) RAMAG-2 and (C) RAMAG-3.

In the RAM assay, activated lymphocytes incubated in the presence of increasing concentrations of RAMAG-1 and the CXCR3 ligand I-TAC at 250 nM, cell migration was activated at less than 1 μM (FIG. 6A); as RAMAG-1 concentration increased, migration increased, reaching approaching a maximum at (0.5 μM to 1 μM) of RAMAG-1.

Figure 5:
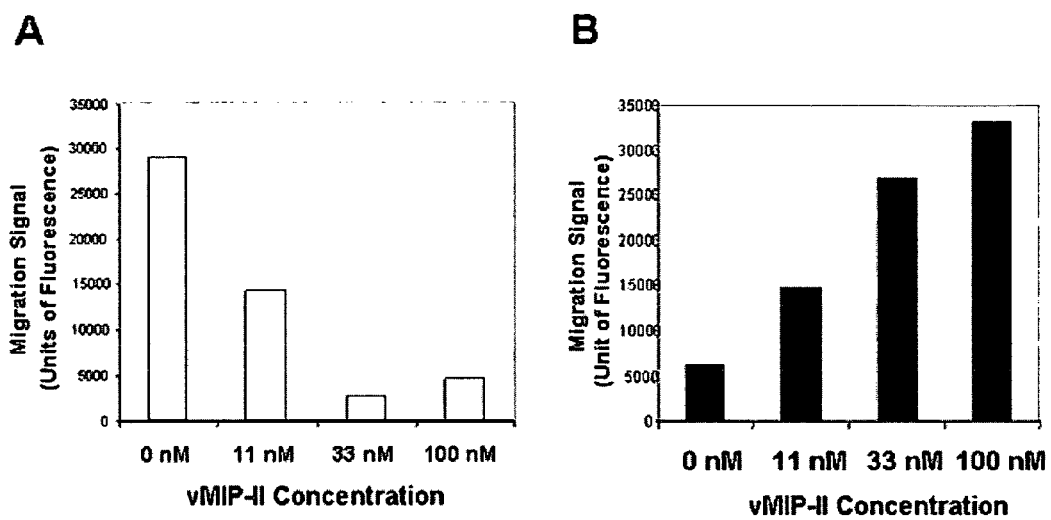
FIG. 5 shows graphs depicting the results from a RAM assay validation experiment using a protein CXCR4 antagonist. Chemokine SDF-1α-mediated cell migration in the presence of the CXCR4 antagonist, vMIP-II, under (A) conventional and (B) RAM conditions.

At a CXCR4 SDF-1α ligand concentration of 100 nM using CXCR4-expressing MOLT-4 cells, RAMAG-2 activated cell migration at 5 μM (FIG. 5, B). As was observed with RAMAG-1, further activation of migration was seen as the RAMAG-2 concentration increased to 10 μM.

The CCR1 antagonist, RAMAG-3 also gave similar results. In a RAM assay using CCR1-expressing THP-1 cells, RAMAG-3 activated cell migration at 100 nM; as RAMAG-3 concentration increased, so did the migration signal (FIG. 5, C).

Example 4

Validation of RAM Assay Using Known Small Molecules that Non-Specifically Inhibit Cell Migration in CXCR4-Bearing Cells in Conventional Assays This experiment conclusively demonstrates the ability of the RAM assay to discern non-specific and specific chemokine receptor antagonists. A conventional and RAM assays were performed as described in Example 2, but with the following candidate antagonists:

(1) control (no candidate antagonist)
(2) positive control (vMIP-II; a known CXCR4 antagonist)
(3) known non-specific inhibitors of cell migration:

compound #1
compound #2
compound #3.

Figure 7:
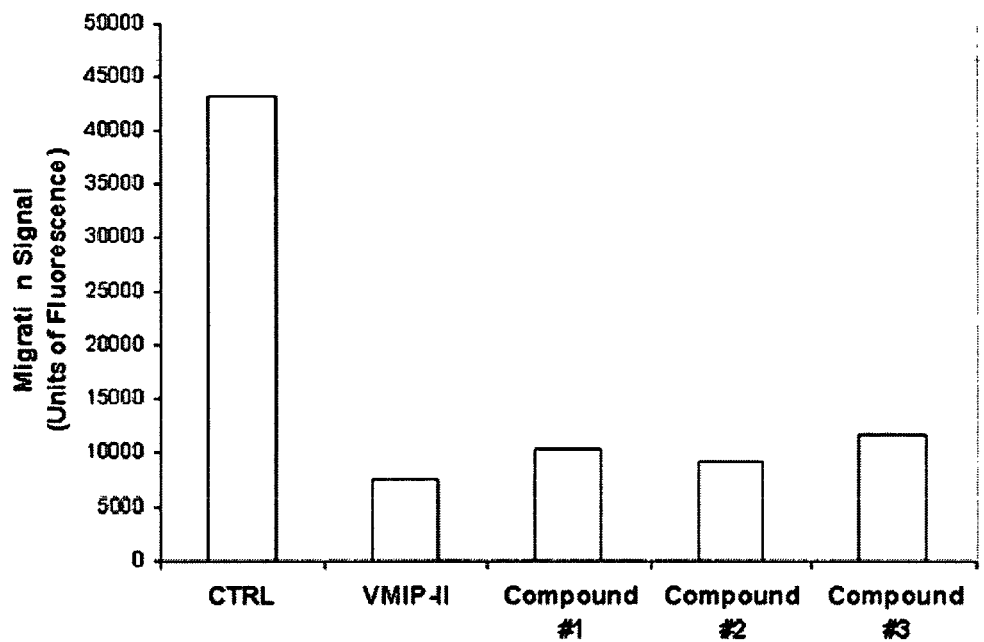
FIG. 7 demonstrates the efficacy of the RAM assay to discern false positive signals. (A) conventional assay, showing inactivation of cell migration by three compounds known to be non-specific; (B) RAM assay, wherein the same three compounds are not indicative of a chemokine receptor antagonist.
Figure 7:
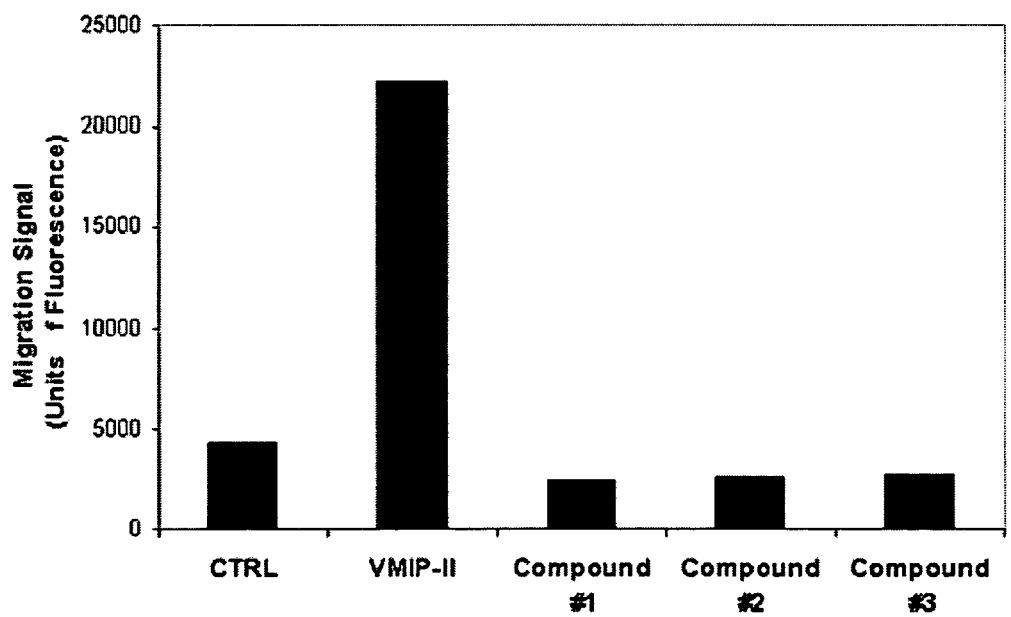

As shown in FIG. 7A, control cells migrated, but those incubated with vMIP-II and compounds #1, #2 and #3 showed decreased cell migration. When these same candidate antagonists were subjected to a RAM assay (FIG. 7B), control cells did not migrate, as expected, while vMIP-II-treated cells did migrate (also expected). However, compounds #1, #2 and #3, known compounds that non-specifically inhibit cell migration in conventional assays, failed to activate cell migration in the RAM assay.

From the results presented in Examples 2-4, the RAM assay distinguishes between non-specific and specific antagonists of chemoattractant receptors, such as chemokine receptors.

Example 5

Determining Inhibitory Concentrations of MIP-1α and MCP-1

To obtain a dose response curve for THP-1 cells expressing cell surface CCR1 and CCR2, a conventional cell migration assay was used (Bacon et al., 1988; Penfold et al., 1999). Cells were harvested by centrifugation and then resuspended in cell migration buffer (Hank's balanced salt solution (HBSS)/ 0.1% bovine serum albumin (BSA)) at $0.1 \times 10^6$ cells per well. The CCR1 and CCR2 ligands MIP-1α and MCP-1, respectively, were prepared in the concentration series (10 nM to 10 μM) by serial dilution in cell migration buffer. At low concentrations, MIP-1α and MCP-1 activate cell migration of CCR1 and CCR2 bearing activated cells, respectively.

MIP-1α and MCP-1 were loaded in the bottom chamber of a ChemoTx® cell migration apparatus (5 μm pore polycarbonate polyvinylpyrrolidone-coated filters (Neuroprobe; Gaithersburg, Md.); 29 μl/well) and 20 μl of cell suspension (100K cell per well) was placed in the upper chamber. The cells were incubated at 37° C. for 90 minutes. The assay was terminated by removing the cells from the upper chamber and membrane surface using a rubber scraper. The cells that migrated to the lower chamber were quantified by CyQuant assay (Molecular Probes; Eugene, Oreg.), a fluorescent dye method that measures nucleic acid content.

Figure 10:
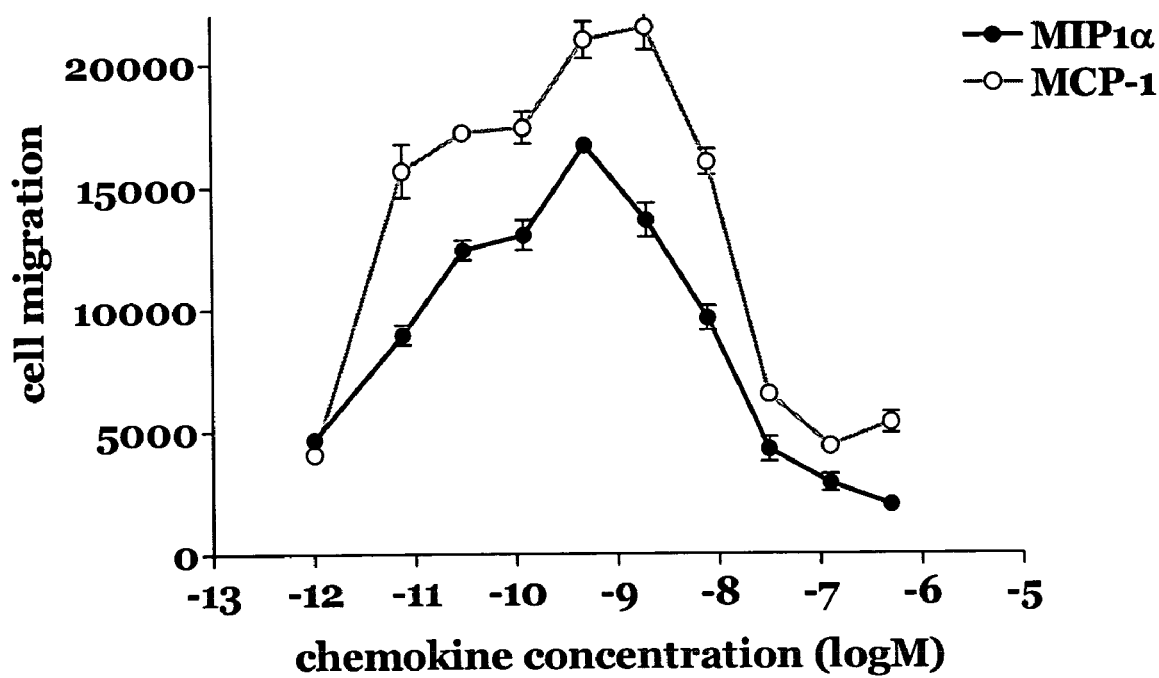
FIG. 10 is a graph depicting the MIP-1α and MCP-1 induced THP-1 cell migration. X-axis, chemokine concentration (logM); Y-axis, cell migration as measured in cell migration assay.

To determine the minimum concentration of MIP-1α and MCP-1 to inhibit cell migration, chemokine concentrations (X-axis) is plotted against relative fluorescent units, correlating to the number of cells migrating (Y-axis) (FIG. 10). Initially as MIP-1α and MCP-1 concentrations increase, cell migration increase linearly; however, at higher concentrations, migration levels first flatten and then decrease, until migration is barely detectable. This bell-shaped curve is typical of chemokine and chemokine receptor-mediated cell migration. In this experiment, 150 nM concentration of MIP-1α and MCP-1 were determined to be completely inhibitory; the inhibitory concentration range was 10 nM to 1 μM.

Example 6

Effects of Full RAM Concentrations of MIP-1α on the Induced Migration of the MCP-1 in a BiRAM Screen To determine whether MIP-1α activity had an effect on the activity of MCP-1, a conventional cell migration as previously described in Example 5 was used (Bacon et al., 1988; Penfold et al., 1999). An effect of 100 nM of MIP-1α on MCP-1 was studied by comparing migration levels of THP-1 cells as activated by MCP-1 with THP-1 cell migration levels as activated by incubation with MCP-1 and 100 nM MIP-1α.

100 nM MIP-1α with MCP-1 at various concentrations were loaded in the bottom chamber of a ChemoTx® cell migration apparatus (5 μm pore polycarbonate polyvinylpyrrolidone-coated filters (Neuroprobe; Gaithersburg, Md.); 29 μl/well) and 20 μl of cell suspension (100K cell per well) was placed in the upper chamber. The cells were incubated at 37° C. for 90 minutes. The assay was terminated by removing the cells from the upper chamber and membrane surface using a rubber scraper. The cells that migrated to the lower chamber were quantified by CyQuant assay (Molecular Probes; Eugene, Oreg.), a fluorescent dye method that measures nucleic acid content.

Figure 11:
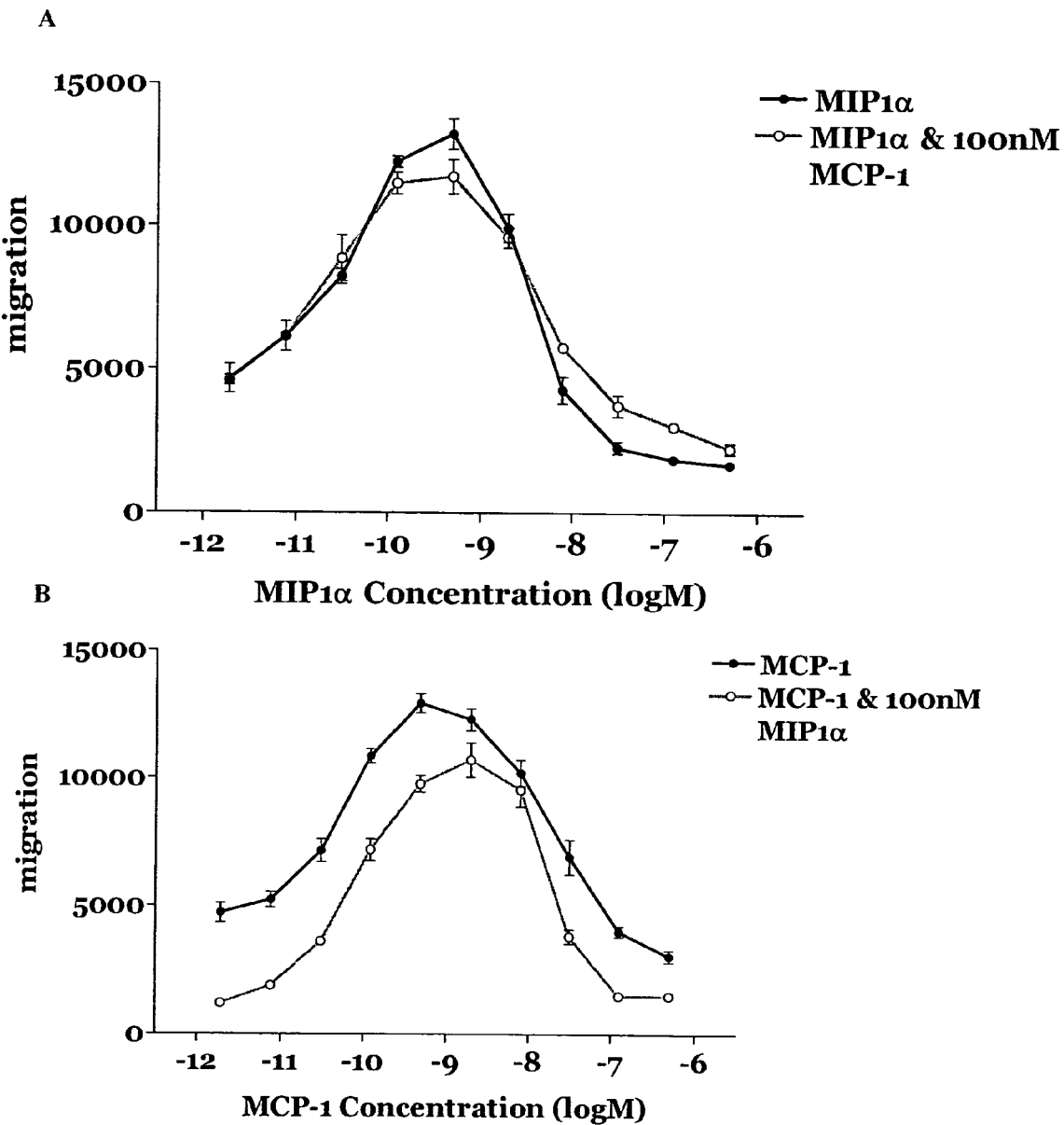
FIG. 11 is a graph of the effect of full RAM concentrations of one chemokine on the induced migration of another chemokine. Effect of 100 nM of MIP-1α on MCP-1-induced cell migration; 100 nM MIP-1α only slightly lowers the overall MCP-1-induced migration of THP-1 cells (A). Effect of 100 nM of MCP-1 on MIP-1α-induced cell migration; 100 nM of MCP-1 has minimal effect on the overall MIP-1α induced migration on the same cells (B). In both cases the overall signal is not significantly affected. X-axis, MCP-1 (A) and MIP-1α (B) concentration (logM); Y-axis, cell migration as measured in cell migration assay.

Referring to FIG. 11A, 100 nM MIP-1α only slightly lowers the overall MCP-1 induced migration of THP-1 cells. There was no significant effect on MCP-1-induced cell migration when cells were treated with 100 nM MIP-1α.

Example 7

Effects of Full RAM Concentrations of MCP-1 on the Migration Induced by MIP-1α Chemokine in a BiRAM Screen To determine whether MCP-1 activity had an effect on the activity of MIP-1α, a conventional cell migration as previously described in Example 5 was used (Bacon et al., 1988; Penfold et al., 1999). An effect of 100 nM of MCP-1 on MIP-1α was studied by comparing migration levels of THP-1 cells as activated by MIP-1α with THP-1 cell migration levels as activated by incubation with MIP-1α and 100 nM MCP-1.

100 nM MCP-1 with MIP-1α at various concentrations were loaded in the bottom chamber of a ChemoTx® cell migration apparatus (5 μm pore polycarbonate polyvinylpyrrolidone-coated filters (Neuroprobe; Gaithersburg, Md.); 29 μl/well) and 20 μl of cell suspension (100K cell per well) was placed in the upper chamber. The cells were incubated at 37° C. for 90 minutes. The assay was terminated by removing the cells from the upper chamber and membrane surface using a rubber scraper. The cells that migrated to the lower chamber were quantified by CyQuant assay (Molecular Probes; Eugene, Oreg.), a fluorescent dye method that measures nucleic acid content.

FIG. 11B demonstrates that MIP-1α and MIP-1α with 100 nM MCP-1 induced cell migration. Referring to FIG. 11B, 100 nM MCP-1 only slightly lowers the overall MIP-1α induced migration of THP-1 cells. There was no significant effect on MIP-1α-induced cell migration when cells were treated with 100 nM MCP-1.

Example 8

Validation of the BiRAM Assay Using Antagonist Compounds

In the BiRAM assay, antagonists of chemokine receptors are identified by simultaneous screening for their ability to activate migration of cells that are incubated with inhibitory chemokine concentrations. THP-1 cells were plated at a concentration of 100K cells per well. To validate the BiRAM assay, BiRAMAG1 was used as CCR1 antagonist; BiRAMAG2 and BiRAMAG3 were used as CCR2 and CCR9 antagonists, respectively. If the CCR1 and CCR2 expressing cells that are immobilized by inhibitory concentrations of MIP-1α and MCP-1, respectively, are activated to migrate in the presence of BiRAMAG1 and BiRAMAG2 with increased migration, this result would verify the BiRAM principle. As a control a conventional cell migration assay was performed (data not shown). In the conventional assay format, cell migration is inhibited by the antagonists according to above described principles.

Activated THP-1 cell population expressing cell surface CCR1 and CCR2 was harvested as previously described in Example 5. A concentration series of BiRAMAG1, BiRAMAG2 and BiRAMAG3 was first mixed with activated THP-1 cells, and each mixture was then placed in the upper chamber of a ChemoTx® cell migration apparatus (5 µm pore polycarbonate polyvinylpyrrolidone-coated filters (Neuroprobe; Gaithersburg, Md.), 29 µl per well); 20 µl of a 150 nM solution of MIP-1α and MCP-1 was placed in the lower chamber. The cells were incubated at 37° C. for 90 minutes. The assay was terminated by removing the cells from the upper chamber and membrane surface using a rubber scraper. The cells that migrated to the lower chamber in response to each of the antagonist compounds were quantified by the CyQuant assay (Molecular Probes).

Figure 12:
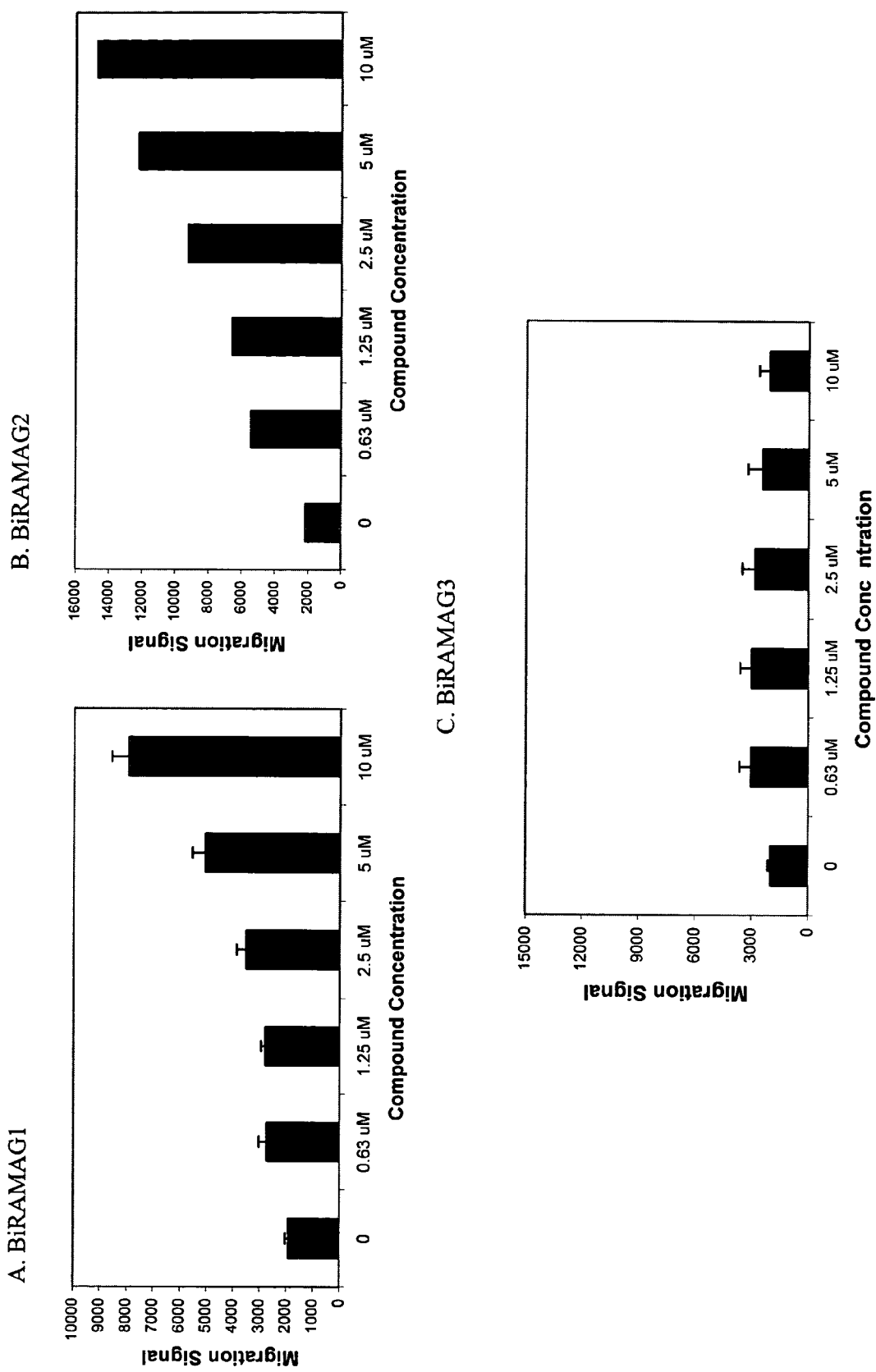
FIG. 12 is a bar graph illustrating the detection of antagonists of both, the CCR1 (A), CCR2 (B). There was no specific activation of cell migration by antagonist to CCX9 receptor (C). MIP-1α and MCP-1 RAM concentrations are 150 nM. BiRAMAG1 is a CCR1 antagonists; BiRAMAG2 is a CCX2 antagonist; BiRAMAG3 is a CCR9 antagonist. X-axis, compound concentration (logM); Y-axis, cell migration as measured in cell migration assay.

In the FIG. 12A, THP-1 cell migration in response to the BiRAMAG1 was observed. In the FIG. 12B, THP-1 cell migration is observed as a result of treatment with CCR2 antagonist, BiRAMAG2. In these instances increased concentration of the respective antagonists positively correlated with an increase in cell migration, with a maximal migration being observed at 10 µM for BiRAMAG1, and 10 µM for BiRAMAG2. Furthermore, cell migration was inhibited across increasing antagonist concentrations in THP-1 cells that were supplemented with a CCR9 antagonist, BiRAMAG3 (FIG. 12C). This is consistent with THP-1 cells lacking the expression of CCR9 on their surface. These results provide support for the BiRAM assay using cell population expressing two chemokine receptors being capable of detecting antagonists of these chemokine receptors. Therefore, this BiRAM assay provides an efficient method of detecting antagonists of both CCR1 and CCR2, which are expressed on THP-1 cells, but not of CCR9 or other receptors, which are not expressed on the surface of these cells.

Example 9

Validation of BiRAM Assay Using Known Small Molecule Antagonists of CCR1 and CCR2

BiRAM screening assays were performed as described in Example 8, except only CCR1 ligand, instead of both CCR1 and CCR2 ligands, was provided.

Activated THP-1 cell population expressing cell surface CCR1 and CCR2 was harvested as previously described in Example 5. A concentration series of BiRAMAG1, BiRAMAG2 and BiRAMAG3 was first mixed with activated THP-1 cells, and each mixture was then placed in the upper chamber of a ChemoTx® cell migration apparatus (5 µm pore polycarbonate polyvinylpyrrolidone-coated filters (Neuroprobe; Gaithersburg, Md.), 29 µl per well); 20 µl of a 10 nM solution of MIP-1α only was placed in the lower chamber. The cells were incubated at 37° C. for 90 minutes. The assay was terminated by removing the cells from the upper chamber and membrane surface using a rubber scraper. The cells that migrated to the lower chamber in response to each of the antagonist compounds were quantified by the CyQuant assay (Molecular Probes).

Figure 13:
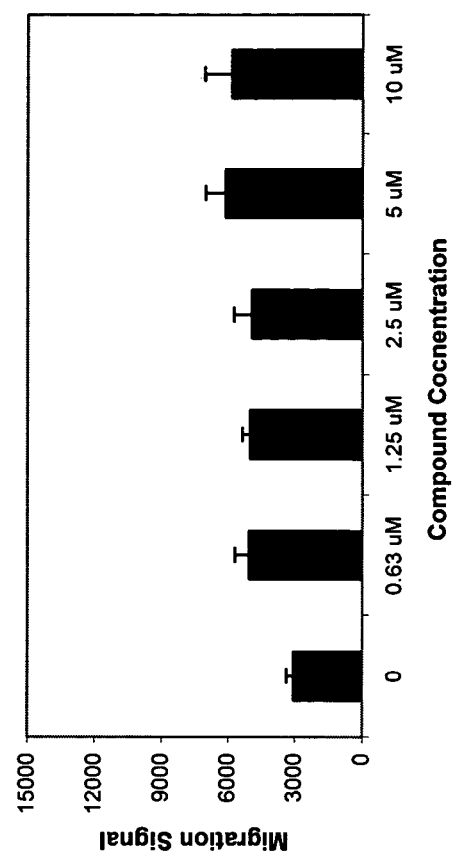
FIG. 13 is a bar graph depicting the results from the validation of BiRAM assay using known small molecule antagonists of CCR1 and CCR2. THP-1 cell expressing CCR1 and CCR2 receptors were provided. CCR1 ligand only was provided. THP-1 cell migration in response to the BiRAMAG1 was observed (A). However, cell migration was inhibited across increasing antagonist concentrations of THP-1 cells that were supplemented with CCR2 antagonist, BiRAMAG2 (B) and CCR9 antagonist, BiRAMAG3 (C). X-axis, compound concentration (logM); Y-axis, cell migration as measured in cell migration assay.
Figure 13:
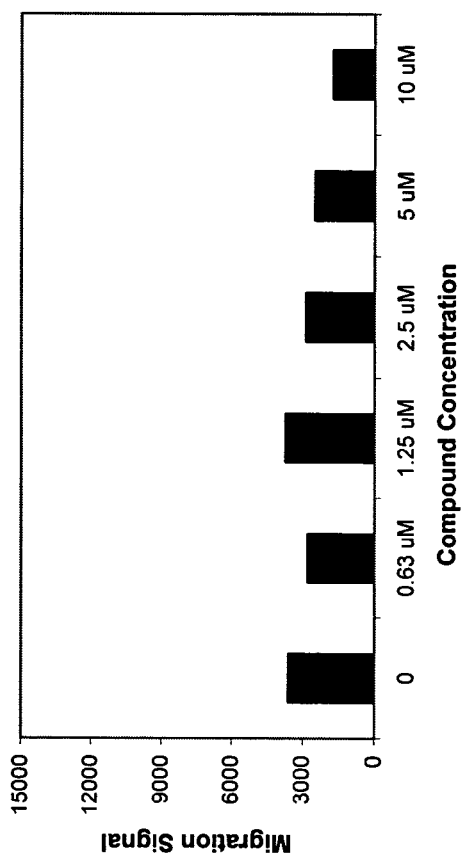
Figure 13:
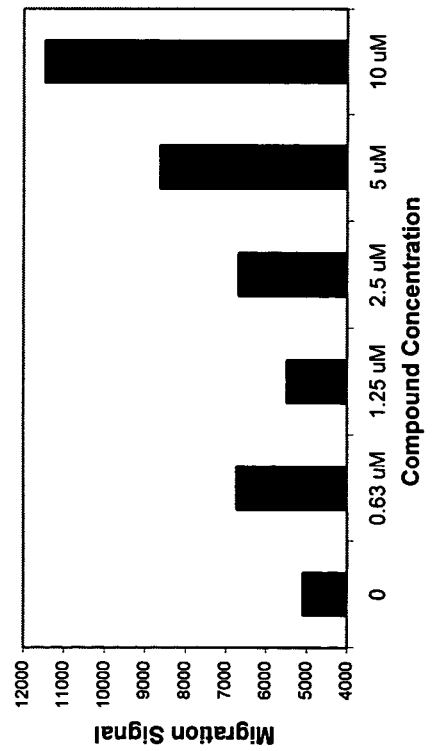

In the FIG. 13A, THP-1 cell migration in response to the BiRAMAG1 was observed. The maximum cell migration was observed at 10 µM for BiRAMAG1. However, cell migration was inhibited across increasing antagonist concentrations in THP-1 cells that were supplemented with a CCR2 antagonist, BiRAMAG2 (FIG. 13B), and CCR9 antagonist, BiRAMAG3 (FIG. 13C). The observed lack of activation of migration of THP-1 cells in response to the treatment with CCR2 antagonist is consistent with lack of the respective chemokine receptor ligand, namely the CCR2 ligand, MCP-1. The latter finding is consistent with THP-1 cells lacking the expression of CCR9 on their surface. These results provide support for the BiRAM assay using cell population expressing two chemokine receptors being capable of detecting antagonists of these chemokine receptors. Therefore, this BiRAM assay provides an efficient method of detecting antagonists of both CCR1 and CCR2, which are expressed on THP-1 cells, provided that the chemokine receptor ligands for respective chemokine receptors are also provided in the assay.

Example 10

Validation of BiRAM Assay Using Known Small Molecule Antagonists of CCR1 and CCR2

BiRAM screening assays were performed as described in Example 8, except only CCR2 ligand, instead of both CCR1 and CCR2 ligands, was provided.

Activated THP-1 cell population expressing cell surface CCR1 and CCR2 receptors was harvested as previously described in Example 5. A concentration series of BiRAMAG1, BiRAMAG2 and BiRAMAG3 was first mixed with activated THP-1 cells, and each mixture was then placed in the upper chamber of a ChemoTx® cell migration apparatus (5 µm pore polycarbonate polyvinylpyrrolidone-coated filters (Neuroprobe; Gaithersburg, Md.), 29 µl per well); 20 µl of a 150 nM solution of MCP-1 only was placed in the lower chamber. The cells were incubated at 37° C. for 90 minutes. The assay was terminated by removing the cells from the upper chamber and membrane surface using a rubber scraper. The cells that migrated to the lower chamber in response to each of the antagonist compounds were quantified by the CyQuant assay (Molecular Probes).

Figure 14:
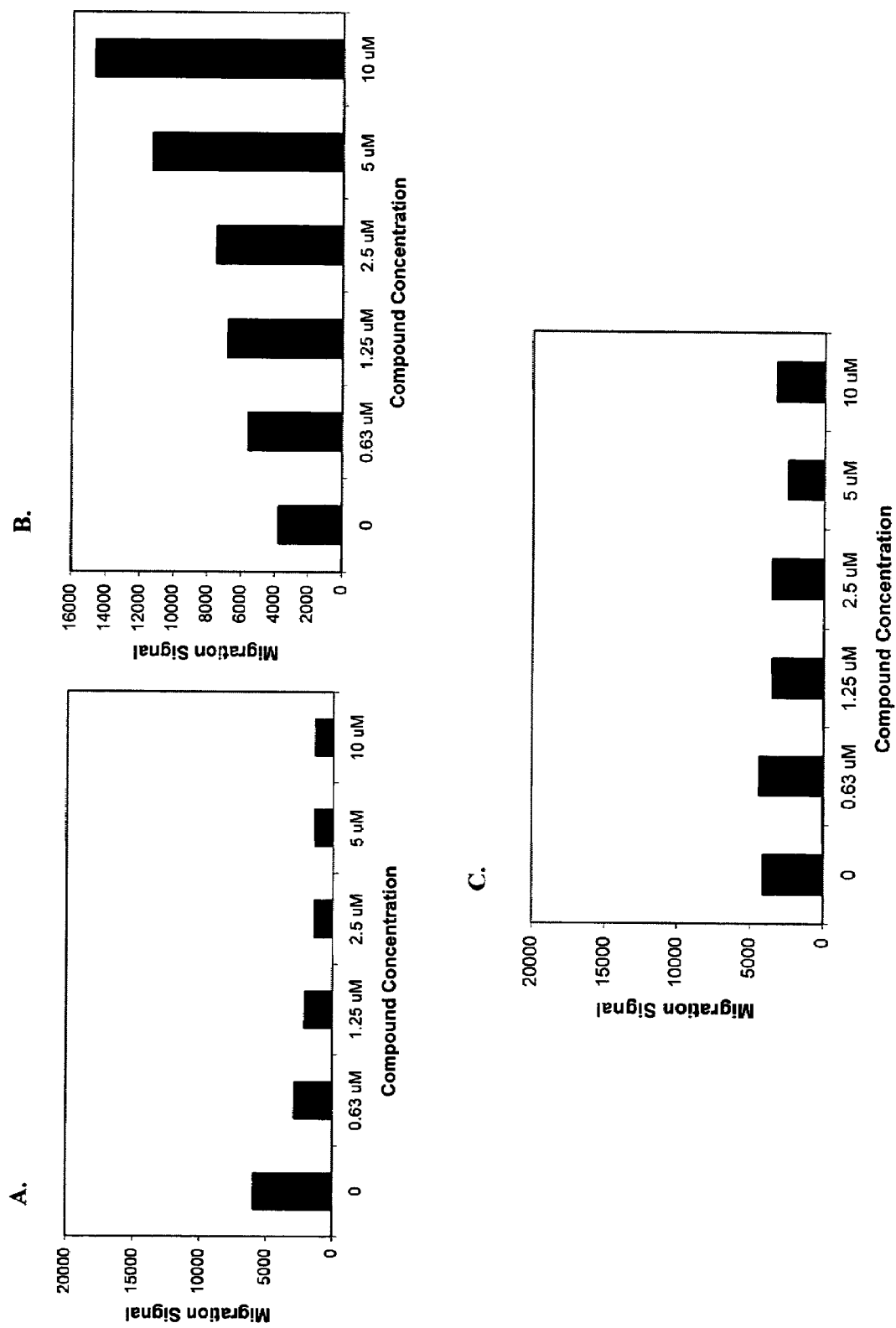
FIG. 14 is a bar graph depicting the results from the validation of BiRAM assay using known small molecule antagonists of CCR1 and CCR2. THP-1 cell expressing CCR1 and CCR2 receptors were provided. CCR2 ligand only was provided. THP-1 cell migration in response to BiRAMAG1 was inhibited across increasing antagonist concentrations (A). There was no migration in response to CCR9 antagonist treatment (C). THP-1 cell migration was observed in response to the CCX2 antagonist, BiRAMAG2 treatment (B). X-axis, compound concentration (logM); Y-axis, cell migration as measured in cell migration assay.

In the FIG. 14A, THP-1 cell migration in response to the BiRAMAG1 was inhibited across increasing antagonist concentrations. The observed inhibition of migration of THP-1 cells in response to the treatment with CCR1 antagonist is consistent with the absence of the respective chemokine receptor ligand, namely the CCR1 ligand, MIP-1α.

In addition, as shown in FIG. 14C, there was no migration observed in cells treated with the CCR9 antagonist, which is consistent with THP-1 cells lacking the expression of CCR9 on their surface.

In addition, as shown in FIG. 14C, there was no migration observed in cells treated with the CCR9 antagonist, which is consistent with THP-1 cells lacking the expression of CCR9 on their surface.

However, cell migration was activated in THP-1 cells that were supplemented with the CCR2 antagonist, BiRAMAG2 (FIG. 14B). These findings validate BiRAM screening assay as an effective method of screening for antagonists of chemokine receptors.

REFERENCES

U.S. Pat. No. 4,816,567. 1989. Recombinant immunoglobin preparations.

Ausubel, F. M., R. Brent, R. E. Kingston, D. D. Moore, et al. 1987. Current protocols in molecular biology. John Wiley & Sons, New York.

Bacon, K. B., R. D. Camp, F. M. Cunningham, and P. M. Woollard. 1988. Contrasting in vitro lymphocyte chemotactic activity of the hydroxyl enantiomers of 12-hydroxy-5,8,10,14-eicosatetraenoic acid. *Br J Pharmacol.* 95:966-74.

Ellington, A. D., and J. W. Szostak. 1990. In vitro selection of RNA molecules that bind specific ligands. *Nature.* 346:818-22.

Forster, R., A. Schubel, D. Breitfeld, E. Kremmer, et al. 1999. CCR7 coordinates the primary immune response by establishing functional microenvironments in secondary lymphoid organs. *Cell.* 99:23-33.

Jayasena, S. D. 1999. Aptamers: an emerging class of molecules that rival antibodies in diagnostics. *Clin Chem.* 45:1628-50.

Jones, P. T., P. H. Dear, J. Foote, M. S. Neuberger, et al. 1986. Replacing the complementarity-determining regions in a human antibody with those from a mouse. *Nature.* 321:522-5.

Kledal, T. N., M. M. Rosenkilde, F. Coulin, G. Simmons, et al. 1997. A broad-spectrum chemokine antagonist encoded by Kaposi's sarcoma-associated herpesvirus. *Science.* 277:1656-9.

Klein, C., J. I. Paul, K. Sauve, M. M. Schmidt, et al. 1998. Identification of surrogate agonists for the human FPRL-1 receptor by autocrine selection in yeast. *Nat Biotechnol.* 16:1334-7.

Penfold, M. E., D. J. Dairaghi, G. M. Duke, N. Saederup, et al. 1999. Cytomegalovirus encodes a potent alpha chemokine. *Proc Natl Acad Sci USA.* 96:9839-44.

Riechmann, L., M. Clark, H. Waldmann, and G. Winter. 1988. Reshaping human antibodies for therapy. *Nature.* 332:323-7.

Rossi, D., and A. Zlotnik. 2000. The Biology of Chemokines and their Receptors. *Annu. Rev. Immunol.* 18:217-242.

Tuerk, C., and L. Gold. 1990. Systematic evolution of ligands by exponential enrichment: RNA ligands to bacteriophage T4 DNA polymerase. *Science.* 249:505-10.

Verhoeyen, M., C. Milstein, and G. Winter. 1988. Reshaping human antibodies: grafting an antilysozyme activity. *Science.* 239:1534-6.

I claim:

1. A method for identifying an antagonist of at least one of first and second chemoattractant receptors, comprising:
   providing an apparatus comprising an upper chamber and a lower chamber separated by a porous membrane;
   placing a candidate antagonist and a cell population comprising the first and second chemoattractant receptors in the upper chamber;
   placing an inhibitory concentration of a ligand for the first chemoattractant receptor in the lower chamber;
   placing an inhibitory concentration of a ligand for the second chemoattractant receptor in the lower chamber; and
   monitoring movement of the cell population from the upper chamber to the lower chamber, wherein the movement identifies the candidate antagonist as an antagonist of at least one of the first and second chemoattractant receptors.

2. The method of claim 1, wherein at least two candidate antagonists are placed with the cell population in the upper chamber.

3. The method of claim 1, wherein the candidate antagonist is a peptide, peptide-like molecule, non-peptidyl organic compound, inorganic compound, nucleic acid or antibody.

4. The method of claim 1, wherein the inhibitory concentration of the ligand for the first chemoattractant receptor inhibits cell migration greater than or equal to about 50% of maximal ligand-activated cell migration.

5. The method of claim 1, wherein the inhibitory concentration of the ligand for the first chemoattractant receptor inhibits cell migration greater than or equal to about 95% of maximal ligand-activated cell migration.

6. The method of claim 1, wherein the inhibitory concentration of the ligand for the first chemoattractant receptor inhibits cell migration greater than or equal to about 100% of maximal ligand-activated cell migration.

7. The method of claim 1, wherein the inhibitory concentration of the ligand for the second chemoattractant receptor inhibits cell migration greater than or equal to about 50% of maximal ligand-activated cell migration.

8. The method of claim 1, wherein the inhibitory concentration of the ligand for the second chemoattractant receptor inhibits cell migration greater than or equal to about 95% of maximal ligand-activated cell migration.

9. The method of claim 1, wherein the inhibitory concentration of the ligand for the second chemoattractant receptor inhibits cell migration greater than or equal to about 100% of maximal ligand-activated cell migration.

10. The method of claim 1, wherein the first and second chemoattractant receptors are each independently a chemokine receptor.

11. The method of claim 10, wherein the chemokine receptor is selected from the group consisting of CCR, CXCR, CX3CR, and XCR classes of chemokine receptors.

12. The method of claim 11, wherein the chemokine receptors are CXCR1, CXCR2, CXCR3, CXCR4, CXCR5, CCR1, CCR2, CCR3, CCR4, CCR5, CCR6, CCR7, CCR8, CCR9, CCR10, CCR11, CX3CR1 or XCR1.

13. The method of claim 1, wherein the ligand for the first chemoattractant receptor is a chemokine.

14. The method of claim 13, wherein the chemokine is selected from the group consisting of CCR, CXCR, and CX3CR receptor ligands.

15. The method of claim 14, wherein the chemokine is IL-8, GCP-2, Gro α, Gro β, Gro γ, ENA-78, PBP, MIG, IP-10, I-TAC, SDF-1α, BLC, MIP-1α, MIP-1β, RANTES, HCC-1, HCC-2, HCC-3, HCC-4, MCP-1, MCP-2, MCP-3, MCP-4, eotaxin-1, eotaxin-2, TARC, MDC, MIP-3α, MIP-3β, 6Ckine, I-309, TECK, lymphotactin, fractalkine, TCA-4, Exodus-2, Exodus-3, or CKβ-11.

16. The method of claim 1, wherein the ligand for the second chemoattractant receptor is a chemokine.

17. The method of claim 16, wherein the chemokine is selected from the group consisting of CCR, CXCR, and CX3CR receptor ligands.

18. The method of claim 17, wherein the chemokine is IL-8, GCP-2, Gro α, Gro β, Gro γ, ENA-78, PBP, MIG, IP-10, I-TAC, SDF-1α, BLC, MIP-1α, MIP-1β, RANTES, HCC-1, HCC-2, HCC-3, HCC-4, MCP-1, MCP-2, MCP-3, MCP-4, eotaxin-1, eotaxin-2, TARC, MDC, MIP-3α, MIP-3β, 6Ckine, I-309, TECK, lymphotactin, fractalkine, TCA-4, Exodus-2, Exodus-3, or CKβ11.

19. The method of claim 1, wherein the ligands for the first and the second chemokine receptors are placed in the lower chamber simultaneously.

20. The method of claim 1, wherein the ligands for the first and the second chemokine receptors are placed in the lower chamber in series.

21. The method of claim 1, wherein the candidate antagonist is placed before at least one of the ligands.

22. The method of claim 1, wherein monitoring movement comprises measuring a signal.

23. The method of claim 22, wherein the signal is a fluorescent signal.

24. The method of claim 1, wherein monitoring movement comprises counting cells using a microscope.

25. The method of claim 1, wherein monitoring movement comprises labeling cells with a marker.

26. The method of claim 25, wherein the marker is a dye or a radioactive label.

27. The method of claim 1, wherein the first and second chemoattractant receptors are selected from the group consisting of C5aR, FPRL1 receptor, CXCR4, CXCR3, CCR1, and CCR9.

28. The method of claim 1, further comprising a step of determining whether an identified antagonist is an antagonist for one of the first chemoattractant receptors, the second chemoattractant receptor, or both.

29. The method of claim 28, wherein determining is performed by a method comprising the steps of:
a) determining whether the identified antagonist is the antagonist for the first chemoattractant receptor comprising the steps of:
  i) placing a second cell population comprising the first chemoattractant receptor with a candidate antagonist in the upper chamber,
  ii) placing an inhibitory concentration of a ligand for the first chemoattractant receptor in the lower chamber, and
  iii) monitoring movement of the second cell population from the upper chamber to the lower chamber, wherein the movement identifies the candidate antagonist as an antagonist of the first chemoattractant receptor; and
b) determining whether the identified antagonist is the antagonist for the second chemoattractant receptor comprising the steps of
  i) placing a third cell population comprising the second chemoattractant receptor with the candidate antagonist in the upper chamber,
  ii) placing an inhibitory concentration of a ligand for the second chemoattractant receptor in the lower chamber, and
  iii) monitoring movement of the third cell population from the upper chamber to the lower chamber, wherein the movement identifies the candidate antagonist as an antagonist of the second chemoattractant receptor.

30. The method of claim 28, wherein determining is performed by calcium mobilization assay or cell migration assay.

31. A method for identifying an antagonist of at least one of first and second chemoattractant receptors, comprising:
providing an apparatus comprising an upper chamber and a lower chamber separated by a porous membrane;
placing a candidate antagonist and a first cell population and a second cell population in the upper chamber, wherein the first cell population comprises the first chemoattractant receptor and wherein the second cell population comprises the second chemoattractant receptor;
placing an inhibitory concentration of a ligand for the first chemoattractant receptor in the lower chamber;
placing an inhibitory concentration of a ligand for the second chemoattractant receptor in the lower chamber; and
monitoring movement of the first and the second cell populations from the upper chamber to the lower chamber, wherein the movement identifies the candidate antagonist as an antagonist of at least one of the first and second chemoattractant receptors.

32. The method of claim 31, wherein at least two candidate antagonists are placed with the first and the second cell populations in the upper chamber.

33. The method of claim 31, wherein the candidate antagonist is a peptide, peptide-like molecule, non-peptidyl organic compound, inorganic compound, nucleic acid or antibody.

34. The method of claim 31, wherein the inhibitory concentration of the ligand for the first chemoattractant receptor inhibits cell migration greater than or equal to about 50% of maximal ligand-activated cell migration.

35. The method of claim 31, wherein the inhibitory concentration of the ligand for the first chemoattractant receptor inhibits cell migration greater than or equal to about 95% of maximal ligand-activated cell migration.

36. The method of claim 31, wherein the inhibitory concentration of the ligand for the first chemoattractant receptor inhibits cell migration greater than or equal to about 100% of maximal ligand-activated cell migration.

37. The method of claim 31, wherein the inhibitory concentration of the ligand for the second chemoattractant receptor inhibits cell migration greater than or equal to about 50% of maximal ligand-activated cell migration.

38. The method of claim 31, wherein the inhibitory concentration of the ligand for the second chemoattractant receptor inhibits cell migration greater than or equal to about 95% of maximal ligand-activated cell migration.

39. The method of claim 31, wherein the inhibitory concentration of the ligand for the second chemoattractant receptor inhibits cell migration greater than or equal to about 100% of maximal ligand-activated cell migration.

40. The method of claim 31, wherein the first and second chemoattractant receptors are each independently a chemokine receptor.

41. The method of claim 40, wherein the chemokine receptor is selected from the group consisting of CCR, CXCR, CX3CR, and XCR classes of chemokine receptors.

42. The method of claim 41, wherein the chemokine receptors are CXCR1, CXCR2, CXCR3, CXCR4, CXCR5, CCR1, CCR2, CCR3, CCR4, CCR5, CCR6, CCR7, CCR8, CCR9, CCR10, CCR11, CX3CR1 or XCR1.

43. The method of claim 31, wherein the ligand for the first chemoattractant receptor is a chemokine.

44. The method of claim 43, wherein the chemokine is selected from the group consisting of CCR, CXCR, and CX3CR receptor ligands.

45. The method of claim 44, wherein the chemokine is IL-8, GCP-2, Gro α, Gro β, Gro γ, ENA-78, PBP, MIG, IP-10, I-TAC, SDF-1α, BLC, MIP-1α, MIP-1β, RANTES, HCC-1, HCC-2, HCC-3, HCC-4, MCP-1, MCP-2, MCP-3, MCP-4, eotaxin-1, eotaxin-2, TARC, MDC, MIP-3α, MIP-3β, 6Ckine, I-309, TECK, lymphotactin, fractalkine, TCA-4, Exodus-2, Exodus-3, or CKβ-11.

46. The method of claim 31, wherein the ligand for the second chemoattractant receptor is a chemokine.

47. The method of claim 46, wherein the chemokine is selected from the group consisting of OCR, OXOR, and CX3CR receptor ligands.

48. The method of claim 47, wherein the chemokine is IL-8, GCP-2, Gro α, Gro β, Gro γ, ENA-78, PBP, MIG, IP-10, I-TAC, SDF-1α, BLC, MIP-1α, MIP-1β, RANTES, HCC-1, HCC-2, HCC-3, HCC-4, MCP-1, MCP-2, MCP-3, MCP-4, eotaxin-1, eotaxin-2, TARC, MDC, MIP-3α, MIP-3β, 6Ckine, I-309, TECK, lymphotactin, fractalkine, TCA-4, Exodus-2, Exodus-3, or CKβ-11.

49. The method of claim 31, wherein the ligands for the first and the second chemoattractant receptor are placed in the lower chamber simultaneously.

50. The method of claim 31, wherein the ligands for the first and the second chemoattractant receptor are placed in the lower chamber in series.

51. The method of claim 31, wherein the at least one candidate antagonist is placed in the apparatus before the at least one of the ligands.

52. The method of claim 31, wherein the monitoring movement comprises measuring a signal.

53. The method of claim 52, wherein the signal is a fluorescent signal.

54. The method of claim 31, wherein monitoring movement comprises counting cells using a microscope.

55. The method of claim 31, wherein monitoring movement comprises labeling cells with a marker.

56. The method of claim 55, wherein the marker is a dye or a radioactive label.

57. The method of claim 31, wherein first and second chemoattractant receptors are selected from the group consisting of C5aR, FPRL1 receptor, CXCR4, CXCR3, CCR1, and CCR9.

58. The method of claim 31, further comprising a step of determining whether an identified antagonist is an antagonist for one of the first chemoattractant receptors, the second chemoattractant receptor, or both.

59. The method of claim 58, wherein determining is performed by a method comprising the steps of:

a) determining whether the identified antagonist is the antagonist for the first chemoattractant receptor comprising the steps of:
  i) placing a first cell population comprising the first chemoattractant receptor and a candidate antagonist in the upper chamber,
  ii) placing an inhibitory concentration of a ligand for the first chemoattractant receptor in the lower chamber, and
  iii) monitoring movement of the first cell population from the upper chamber to the lower chamber, wherein the movement identifies the candidate antagonist as an antagonist of the first chemoattractant receptor; and b) determining whether the identified antagonist is the antagonist for the second chemoattractant receptor comprising the steps of:
  i) placing a second cell population comprising the second chemoattractant receptor and the candidate antagonist in the upper chamber,
  ii) placing an inhibitory concentration of a ligand for the second chemoattractant receptor in the lower chamber, and
  iii) monitoring movement of the second cell population from the upper chamber to the lower chamber, wherein the movement identifies the candidate antagonist as an antagonist of the second chemoattractant receptor.

60. The method of claim 58, wherein determining is performed by calcium mobilization assay or cell migration assay.

* * * * *